US00RE49302E

(19) United States
(12) Reissued Patent
Sarkar et al.

(10) Patent Number: US RE49,302 E
(45) Date of Reissued Patent: *Nov. 15, 2022

(54) PHARMACEUTICAL FORMULATIONS CONTAINING DOPAMINE RECEPTOR LIGANDS

(71) Applicant: Richter Gedeon Nyrt., Budapest (HU)

(72) Inventors: Ranajoy Sarkar, Skillman, NJ (US); Mahendra G. Dedhiya, Pomona, NY (US); Anil Chhettry, Holtsville, NY (US)

(73) Assignee: Richter Gedeon Nyrt., Budapest (HU)

( * ) Notice: This patent is subject to a terminal disclaimer.

(21) Appl. No.: 16/384,264

(22) Filed: Apr. 15, 2019

Related U.S. Patent Documents

Reissue of:
(64) Patent No.: 9,056,846
Issued: Jun. 16, 2015
Appl. No.: 13/653,576
Filed: Oct. 17, 2012

U.S. Applications:
(63) Continuation of application No. 15/598,971, filed on May 18, 2017, now Pat. No. Re. 47,350, which is an application for the reissue of Pat. No. 9,056,846, which is a continuation of application No. 12/504,149, filed on Jul. 16, 2009, now Pat. No. 9,056,845.

(60) Provisional application No. 61/081,052, filed on Jul. 16, 2008.

(51) Int. Cl.
*H04N 5/378* (2011.01)
*H04N 5/374* (2011.01)

(52) U.S. Cl.
CPC ..... *H04N 5/378* (2013.01); *H04N 5/374* (2013.01)

(58) Field of Classification Search
CPC ..... H04N 5/378; H04N 5/374
See application file for complete search history.

(56) References Cited

U.S. PATENT DOCUMENTS

| | | | |
|---|---|---|---|
| 4,666,911 | A | 5/1987 | Fujimura et al. |
| 4,943,632 | A | 7/1990 | Robinson |
| 4,957,921 | A | 9/1990 | Caprathe et al. |
| 5,384,323 | A | 1/1995 | Bolz |
| 5,807,575 | A | 9/1998 | Dumoulin |
| 5,846,514 | A | 12/1998 | Foster et al. |
| 5,910,319 | A | 6/1999 | Anderson et al. |
| 6,334,997 | B1 | 1/2002 | Foster et al. |
| 6,395,739 | B1 | 5/2002 | Sato et al. |
| 6,489,341 | B1 | 12/2002 | Jerussi |
| 6,528,529 | B1 | 3/2003 | Brann et al. |
| 6,566,550 | B2 | 5/2003 | Lowe, III |
| 6,667,060 | B1 | 12/2003 | Vandecruys |
| 6,919,342 | B2 | 7/2005 | Haupt |
| 7,122,576 | B2 | 10/2006 | Plata-Salaman et al. |
| 7,737,142 | B2 | 6/2010 | Csongor et al. |
| 7,829,569 | B2 | 11/2010 | Liao et al. |
| 7,875,610 | B2 | 1/2011 | Szalai et al. |
| 7,943,621 | B2 | 5/2011 | Czibula et al. |
| 7,981,897 | B2 | 7/2011 | Bathe et al. |
| 8,569,496 | B2 | 10/2013 | Czibula et al. |
| 8,569,497 | B2 | 10/2013 | Czibula et al. |
| 8,569,498 | B2 | 10/2013 | Czibula et al. |
| 8,765,765 | B2 | 7/2014 | Csongor et al. |
| 8,802,672 | B2 | 8/2014 | Szalai et al. |
| 8,802,888 | B2 | 8/2014 | Mathe et al. |
| 8,846,100 | B2 | 9/2014 | Shojaei |
| 9,056,845 | B2 | 6/2015 | Sarkar et al. |
| 9,056,846 | B2 | 6/2015 | Sarkar et al. |
| RE47,333 | E | 4/2019 | Sarkar et al. |
| RE47,350 | E | 4/2019 | Sarkar et al. |
| 2001/0009912 | A1 | 7/2001 | Tsaklakidis et al. |
| 2003/0144285 | A1 | 7/2003 | Brann et al. |
| 2004/0259882 | A1 | 12/2004 | Haupt et al. |
| 2005/0107397 | A1 | 5/2005 | Galambos et al. |
| 2006/0229297 | A1 | 10/2006 | Csongor et al. |
| 2007/0099931 | A1 | 5/2007 | Ghosh et al. |
| 2007/0244093 | A1 | 10/2007 | Boehm et al. |
| 2007/0259885 | A1 | 11/2007 | Bathe et al. |
| 2009/0023750 | A1 | 1/2009 | Czibula et al. |
| 2009/0036468 | A1 | 2/2009 | Samoriski et al. |
| 2010/0016334 | A1 | 1/2010 | Sarkar |
| 2010/0137335 | A1 | 6/2010 | Csongor et al. |
| 2010/0197666 | A1 | 8/2010 | Laszlovsky et al. |
| 2010/0197704 | A1 | 8/2010 | Laszlovsky et al. |
| 2010/0256145 | A1 | 10/2010 | Bak-Jensen et al. |
| 2011/0059980 | A1 | 3/2011 | Oobayashi |
| 2011/0269959 | A1 | 11/2011 | Csongor et al. |
| 2011/0275804 | A1 | 11/2011 | Czibula et al. |
| 2011/0275816 | A1 | 11/2011 | Czibula et al. |

(Continued)

FOREIGN PATENT DOCUMENTS

| | | |
|---|---|---|
| CN | 105218484 | 1/2016 |
| CN | 105330616 | 2/2016 |

(Continued)

OTHER PUBLICATIONS

Abraham, Ed., "History of Quantitative Structure-Activity Relationships," Burger's Medicinal Chemistry and Drug Discovery, 6th edition, vol. 1, pp. 1-48, (Jan. 2003).

Aiken, "Pramipexole in psychiatry: A systematic review of the literature," *J. Clin Psychiatry*., 68(8):1230-1236, (2007).

Alphs et al, "Asenapine in the Treatment of Negative Symptoms of Schizophrenia: Clinical Trial Design and Rationale Psychopharmacology Bulletin," 2007, 40(2):41-53.

Archer and Kostrzewa, "Neuroteratology and Animal Modeling of Brain Disorders," Neurotoxin Modeling of Brain Disorders—Lifelong Outcomes in Behavioral Teratology, 2015, pp. 1-40.

Artursson et al., "Correlation between oral drug absorption in humans and apparent drug permeability coefficients in human intestinal epithelial (Caco-2) cells," Biochem. Biophys. Res. Comm., 1991, 175(3):880-885.

(Continued)

*Primary Examiner* — Dwayne C. Jones
(74) *Attorney, Agent, or Firm* — Fish & Richardson P.C.

(57) ABSTRACT

The present invention relates to stable and bioavailable immediate release formulations comprising dopamine receptor ligands. Methods of treating various disorders by administering the formulations are also described.

5 Claims, No Drawings

(56) References Cited

U.S. PATENT DOCUMENTS

| | | | |
|---|---|---|---|
| 2011/0288329 | A1 | 11/2011 | Mathe et al. |
| 2013/0040966 | A1 | 2/2013 | Sarkar |
| 2015/0306094 | A1 | 10/2015 | Pitter |
| 2020/0222391 | A1 | 7/2020 | Konta et al. |
| 2020/0323842 | A1 | 10/2020 | Roman et al. |
| 2021/0276965 | A1 | 9/2021 | Neu et al. |

FOREIGN PATENT DOCUMENTS

| | | |
|---|---|---|
| EP | 0224751 | 10/1987 |
| EP | 0453574 | 10/1991 |
| EP | 0431580 | 3/1995 |
| EP | 2251011 | 11/2010 |
| EP | 16165247 | 10/2017 |
| JP | 01-199977 | 8/1989 |
| JP | 01-308284 | 12/1989 |
| JP | 04-275280 | 9/1992 |
| JP | 05-032586 | 2/1993 |
| JP | 05-310745 | 11/1993 |
| KR | 20050043131 | 5/2005 |
| WO | WO 1991/07411 | 5/1991 |
| WO | WO 1997/011070 | 3/1997 |
| WO | WO 1999/050247 | 10/1999 |
| WO | WO 1999/067206 | 12/1999 |
| WO | WO 2001/005763 | 1/2001 |
| WO | WO 2003/029233 | 4/2003 |
| WO | WO 2003/064393 | 8/2003 |
| WO | WO 2005/012266 | 2/2005 |
| WO | WO 2006/034774 | 4/2006 |
| WO | WO 2006/044524 | 4/2006 |
| WO | WO 2006/082456 | 8/2006 |
| WO | WO 2007/033191 | 3/2007 |
| WO | WO 2008/038003 | 4/2008 |
| WO | WO 2008/139235 | 11/2008 |
| WO | WO 2008/141135 | 11/2008 |
| WO | WO 2008/142461 | 11/2008 |
| WO | WO 2008/142462 | 11/2008 |
| WO | WO 2009/020897 | 2/2009 |
| WO | WO 2009/104739 | 8/2009 |
| WO | WO 2010/009309 | 1/2010 |
| WO | WO 2010/070368 | 6/2010 |
| WO | WO 2010/070369 | 6/2010 |
| WO | WO 2010/126527 | 11/2010 |
| WO | WO 2011/060363 | 5/2011 |
| WO | WO 2013/169101 | 11/2013 |
| WO | WO 2014/031162 | 2/2014 |
| WO | WO 2014/083522 | 6/2014 |
| WO | WO 2015/056164 | 4/2015 |
| WO | WO 2015/086836 | 6/2015 |

OTHER PUBLICATIONS

Auclair et al., "P.3.c. Psychotic disorders and treatment—Treatment (basic)" World Congress of The International College of Neuropsychopharmacology, 2014, 1 page.

Baldessarini and Tarazi, "Pharmacotherapy of Psychosis and Mania," Brunton et al. (eds.), Goodman and Gilman's The Pharmacological Basis of Therapeutics, 11th Edition, McGraw Hill, Chapter 18, pp. 461-500, (2005).

Bambini-Junior et al., "Animal model of autism induced by prenatal exposure to valproate: behavioral changes and liver parameters," Brain Res., Aug. 2011, 1408:8-16.

Barnes et al., "Evidence-based guidelines for the pharmacological treatment of schizophrenia: recommendations from the British Association for Psychopharmacology," *J Psychopharmacol*., 25(5):567-620, (Epub Feb. 3, 2011).

Belliotti et al., "Novel Cyclohexyl Amides as Potent and Selective 0 3 Dopamine Receptor Liqands," Bioorq. Med. Chem. Lett., 1997, 7(18):2403-2408.

Berge et al., "Pharmaceutical salts," Journal of Pharmaceutical Sciences, 66(1):1-19 (1977).

Bézard et al., "Attenuation of levodopa-induced dyskinesia by normalizing dopamine D3 receptor function," *Nat. Med*., 9(6):762-767, (2003).

Brugha et al., "Epidemiology of autism spectrum disorders in adults in the community in England," Arch. Gen. Psychiatry., May 2011, 68(5)459-65.

Buchanan et al., "Asenapine Versus Olanzapine in People With Persistent Negative Symptoms of Schizophrenia," Journal of Clinical Psychopharmacology, Feb. 2012, 32:1:36-45.

Carpenter et al., "Treatment of negative symptoms," *Schizophr Bull*., 11(3)440-452, 1985.

CDC "Prevalence of Autism Spectrum Disorder Among Children Aged 8 Years—Autism and Developmental Disabilities Monitoring Network," Morbidity and Mortality Weekly Report Surveillance Summaries, 2018, 67(6):1-23.

Chadman, "Fluoxetine but not risperidone increases sociability in the BTBR mouse model of autism," Pharmacol. Biochem. Behav., Jan. 2011, 97(3):586-94.

Chen et al., "A New and Practical Synthesis of Cariprazine through the Facile Construction of 2-[trans-4-(3,3 Dimethylureido)cyclohexyl] acetic Acid," Synthesis, Jun. 2016, 48(18):A-G.

Christensen et al., "Prenatal valproate exposure and risk of autism spectrum disorders and childhood autism," Jama, Apr. 2013, 309(16):1696-703.

ClinicalTrials.gov, NCT02165098, "Cariprazine: Comparison of Slow- and Immediate-Release Forms," dated Mar. 24, 2016, 6 pages.

Creese et al., "Species variation in dopamine receptor binding," Eur. J. Pharmacol., 60:55-66, (1979).

Damasio, "Alzheimer's Disease and Related Dementias," Cecil Textbook of Medicine, 20th Edition, vol. 2, pp. 1992-1996, (1996).

de Berardis, et al., "The novel antipsychotic cariprazine (RGH-188): state-of-the-art in the treatment of psychiatric disorders," Current Pharmaceutical Design, 2016, 22(33):5044-5162.

Dean, [Editor]. "Recent Advances in the Synthesis and Applications of Radiolabeled Compounds for Drug Discovery and Development," Curr., Pharm. Des., vol. 6, No. 10, [Table of Contents] CAN 133:68895 AN 2000:473538 CAPLUS; 3 pages, (2000).

Deshpande et al., "Design and evaluation of oral bioadhesive controlled release formulations of miglitol, intended for prolonged inhibition of intestinal α-glucosidases and enhancement of plasma glucagon like peptide-1 levels," International Journal of Pharmaceutics, 2009, 380(1-2)16-24.

Di Chiara, "Drug addiction as dopamine-dependent associative learning disorder," Eur. J. Pharmacol., 375: 13-30, (1999).

Eli Lilly and Company, "Zyprexa Olanzapine Tablets . . . " MedWatch Safety Alerts for Human Medical Products, FDA [online]. Retrieved from the Internet:< URL: http://www.fda.gov/medwatch/safety/2006/Aug_PIs/Zyprexa_PI.pdf>, 31 pages, (2004).

Elsabbagh et al., "Global prevalence of autism and other pervasive developmental disorders," Autism research, Jun. 2012, 5(3):160-179.

EP Search Report in European Appln. No. PCT/HU2009/000107, dated May 27, 2010, dated May 27, 2010, 3 pages.

Evans, "Synthesis of radiolabeled compounds," J. Radioanal. Chem., 64(1-2):9-32, (1981).

Gandal et al., "Validating γ oscillations and delayed auditory responses as translational biomarkers of autism," Biological psychiatiy, Dec. 2010, 68(12):1100-1106.

Glase et al., "4-bromo-1-methoxy-N-[2-(4-aryl-1-piperazinyl)ethyl]-2-naphthalenecarboxamides: Selective dopamine D3 receptor partial agonists," Bioorganic & Medicinal Chemistry Letters, 6(12):1361-1366, (1996).

Goodwin et al., "Medical Treatment of Acute Bipolar Depression," Manic-Depressive Illness, New York: Oxford University Press, pp. 639-651, (1990).

Grabovac et al., "Comparison of the mucoadhesive properties of various polymers," Advanced Drug Delivery Reviews, 2005, 57(11):1713-1723.

Graff-Guerrero et al., "The effect of antipsychotics on the high-affinity state of D2 and D3 receptors: a positron emission tomography study With [11C]-(+)-PHNO," Arch. Gen. Psychiatry, Jun. 2009, 66(6):606-615.

(56) References Cited

OTHER PUBLICATIONS

Greengrass et al., "Binding characteristics of 3H-prazosin to rat brain alpha-adrenergic receptors," Eur. J. Pharmacol., 55(3):323-326, (1979).
Grunder et al., "Brain and plasma pharmacokinetics of aripiprazole in patients with schizophrenia: an [18F] fallypride PET study," Am. J. Psychiatry, Aug. 2008, 165(8):988-995.
Guérémy et al., "2-Amino-6-chloro-4-(N-methylpiperazino)pyrimidines, inhibitors of spiroperidol binding," J. Med. Chem., 1982, 25(12): 1459-1465.
Gurevich et al., "Mesolimbic dopamine D3 receptors and use of antipsychotics in patients with schizophrenia. A postmortem study." Arch Gen Psychiatry., 54(3):225-232, (1997).
Gurevich et al., "Distribution of dopamine D3 receptor expressing neurons in the human forebrain: comparison with D2 receptor expressing neurons," Neuropsychopharmacology, 20(1):60-80, (Jan. 1999).
Guy et al., ECDEU Assessment Manual for Psychopharmacology. Rockville, Md: US Department of Health, Education, and Welfare, pp. 218-222, Publication ADM 76-338, (1976).
Gyertyan et al., Effects of RGH-237 [N-{4-[4-(3-Aminocarbonyl-phenyl)-piperazin-1-yl]-butyl}-4-bromo-benzamide], an Orally Active, Selective Dopamine D3 Receptor Partial Agonist in Animal Models of Cocaine Abuse, Journal of Pharmacology and Experimental Therapeutics., Mar. 2007, 320(3): 1268-78.
Gyertyan et al., "RGH-790, A selective dopamine D3/D2 receptor partial agonist with cognitive enhancer properties," World Psychiatric Association International Conference, Prague, 1 page [poster], (Oct. 17-21, 2012).
Gyertyán et al., "Subnanomolar dopamine D3 receptor antagonism coupled to moderate D2 affinity results in favourable antipsychotic-like activity: Behavioral Data," Int. J. Neuropsychopharmacol., 5 Suppl. 1:S174, Abstract No. P.3.W.071, (2002).
Gyertyan et al., "Effects of dopamine $D_3$ receptor antagonists on spontaneous and agonist-reduced motor activity in NMRI mice and Wistar rats: comparative study with nafadotride, U 99194A and SB 277011," Behavioural Pharmacology, 15(4):253-262, (2004).
Gyertyán et al., "The selective dopamine D3 receptor antagonists, SB 277011-A and S 33084 block haloperidol-induced catalepsy in rats," Eur. J. Pharmacol., 572:171-174, (2007).
Han et al., "Advances in Characterization of Pharmaceutical Hydrates," Trends in Bio/Pharmaceutical Industry, 2006, 2(3):25-29.
Hara et al., "Risperidone and aripiprazole alleviate prenatal valproic acid-induced abnormalities in behaviors and dendritic spine density in mice," Psychopharmacology (Berl), Nov. 2017, 234(21):3217-3228.
Heidbreder et al., "The role of central dopamine D3 receptors in drug addiction: a review of pharmacological evidence," Brain Res. Rev., 49:77-105, (2005).
Heusler et al., "In vitro profile of the new antipsychotic, F17464, at recombinant human neurotransmitter receptors," Eur. Neuropsychopharm. 2016, 26(S2):S490-S491.
Ichikawa et al., "Aripiprazole in the Treatment of Irritability in Children and Adolescents with Autism Spectrum Disorder in Japan: A Randomized, Double-blind, Placebo-controlled Study," Child Psychiatiy Hum. Dev., Oct. 2017, 48(5):796-806.
Janssen, "Risperdal Consta (risperidone) Long-Acting Injection," MedWatch Safety Alerts for Human Medical Products, FDA [online] Retrieved from the Internet:< URL: http://www.fda.gov/medwatch/safety/2006/Sep_PIs/RisperdalConsta_PI.pdf>, 39 pages (2006).
Joyce, "Dopamine D3 receptor as a therapeutic target for antipsychotic and antiparkinsonian drugs," Pharmacol Ther., 90:231-259, (2001).
Kabalka and Varma, "The synthesis of radiolabeled compounds via organometallic intermediates," Tetrahedron, 45(21):6601-6621, (1989).
Kay et al., "The positive and negative syndrome scale (PANSS) for schizophrenia," Schizophr. Bull., 13:261-276, (1987).
Keck, "The management of acute mania," British Medical Journal, 327(7422):1002-1003, (2003).
Kelley et al., "Empirical validation of primary negative symptoms: independence from effects of medication and psychosis," Am J Psychiatry., 156:406-411, 1996.
King and Schwartz, "Oral solid dosage forms," Remington's Pharmaceutical Sciences, Gennaro, A., Ed., 17th Edition, Mack Publishing Company, Easton PA, Chapter 90, pp. 1603-1632, (1985).
Kiss et al., "Cariprazine (RGH-188), a dopamine D(3) receptor-preferring, D(3)/D(2) dopamine receptor antagonist-partial agonist antipsychotic candidate: in vitro and neurochemical profile," J. Pharmacol. Exp. Ther., Apr. 2010, 333(1):328-40.
Krause et al., "Antipsychotic drugs for patients with schizophrenia and predominant or prominent negative symptoms: a systematic review and metaanalysis," European Archives of Psychiatry and Clinical Neuroscience, Oct. 2018, 268(7):625-639.
Laszy et al., "Dopamine D3 receptor antagonists improve the learning performance in memory impaired rats," Psychopharmacol., 179(3):567-575, (2005).
Layzer, "Degenerative Diseases of the Nervous System," Cecil Textbook of Medicine, 20th Edition, vol. 2, pp. 2050-2057, (1996).
Le Foll et al., "Dopamine D3 receptor ligands for the treatment of tobacco dependence," Expert Opin Investig Drugs, 16(1):45-57, (2007).
LeClerc et al., "Pharmacological therapies for autism spectrum disorder: a review," P. T., Jun. 2015, 40(6):389-397.
Lehman et al., "Practice guideline for the treatment of patients with schizophrenia, second edition," Am. J. Psychiatry, 161(2 Suppl):1-56, (2004).
Lehr et al., "Lectin-mediated drug delivery: The second generation of bioadhesives," Journal of Controlled Release, 2000, 65(1-2):19-29.
Lenert et al., "Public preferences for health states with schizophrenia and a mapping function to estimate utilities from positive and negative symptom scale scores," Schizophr Res., 71(1): 155-165, (Nov. 1, 2004).
Leucht et al., "Second-generation versus first-gerneration antipsychotic drugs for schizophrenia: a meta-analysis," Lancet, 2009, 373:31-41.
Lim et al., "Pharmacological rescue of Ras signaling, GluAl-dependent synaptic plasticity, and learning deficits in a fragile X model," Genes Dev., Feb. 2014, 28(3):273-289.
Ludwig et al., "The use of mucoadhesive polymers in ocular drug delivery," Advanced Drug Delivery Reviews, 2005, 57(11): 1595-1639.
Mailman et al., "Third generation antipsychotic drugs: partial agonism or receptor functional selectivity?" Curr Pharm Des., 2010, 16(5):488-501.
Maj et al., "Effect of antidepressant drugs administered repeatedly on the dopamine D3 receptors in the rat brain," Eur. J. Pharmacol. 351:31-37, (1998).
Martineau et al., "Catecholaminergic metabolism and autism," Dev. Med. Child. Neurol., Aug. 1994, 36(8):688-697.
McBride et al., "Serotonergic Responsivity in Male Young Adults With Autistic Disorder," Results of a pilot study: Arch. Gen. Psychiatry., Mar. 1989, 46(3):213-21.
Millan et al., "S33084, a novel, potent, selective, and competitive antagonist at dopamine D(3)-receptors: II. Functional and behavioral profile compared with GR218,231 and L741,626," J. Pharmacol. Exp. Ther., 293:1063-1073, (2000).
Millan et al., "The dopamine D3 receptor antagonist, (+)-S 14297, blocks the cataleptic properties of haloperidol in rats," Eur. J. Pharmacol., 321:R7-R9, (1997).
Montgomery and Asberg, "A new depression scale designed to be sensitive to change," Br. J. Psychiatry, 134:382-389, (1979).
Morissette et al., "High-throughput crystallization: polymorphs, salts, co-crystals and solvates of pharmaceutical solids," Adv Drug Deliv Rev. 56(3):275-300, Feb. 2004.
Mueser and McGurk, "Schizophrenia," Lancet, 363:2063-2072, (2004).
Müller-Oerlinghausen et al., "Bipolar disorder," Lancet, 359(9302):241-247, (2002).
Muly et al., "Relationship between dose, drug levels, and D2 receptor occupancy for the atypical antipsychotics risperidone and paliperidone," J Pharmacol Exp Ther, Apr. 2012, 341(l):81-9.

(56) References Cited

OTHER PUBLICATIONS

Murphy et al., "Autism spectrum disorder in adults: diagnosis, management, and health services development." Neuropsychiatr Dis Treat, Jul. 2016, 12:1669-86.
Nassar et al., "Improving the decision-making process in structural modification of drug candidates: reducing toxicity," Drug Discov Today, 9(24):1055-1064, (Dec. 2004).
Nassar et al., "Improving the decision-making process in the structural modification of drug candidates: enhancing metabolic stability," Drug Discov Today., 9(23):1020-1028, (Dec. 2004).
Nemeth et al., "Cariprazine versus risperidone monotherapy for treatment of predominant negative symptoms in patients with schizophrenia: a randomised, double-blind, controlled trial," Lancet., 389:1103-1113, Mar. 18, 2017.
Nyberg et al., "Positron emission tomography of in-vivo binding characteristics of atypical antipsychotic drugs. Review of D2 and 5-HT2 receptor occupancy studies and clinical response," Br. J. Psychiatry. Suppl., 29:40-44, (1996).
Oblak et al., "Reduced serotonin receptor subtypes in a limbic and a neocortical region in autism," Autism Res., Dec. 2013, 6(6):571-583.
Pacher and Kecskeméti, "Cardiovascular side effects of new antidepressants and antipsychotics: new drugs, old concerns?" Curr. Pharm. Des., 10(20):2463-2475, (2004).
Papp and Wieronska, "Antidepressant-like activity of amisulpride in two animal models of depression," J. Psychopharmacol., 14:46-52, (2000).
PCT International Preliminary Report on Patentability in International Appln. No. PCT/IB2018/054227, dated Dec. 17, 2019, 8 pages.
PCT International Search Report and Written Opinion in International Appln. No. PCT/IB2018/054227, dated Sep. 20, 2018, 12 pages.
PCT International Search Report in International Appln. No. PCT/HU04/00056, dated Nov. 11, 2004.
PCT International Search Report in International Appln. No. PCT/IB2017/054094, dated Oct. 26, 2017, 7 pages.
Penagarikano et al., "Absence of CNTNAP2 leads to epilepsy, neuronal migration abnormalities, and core autism-related deficits," Cell, Sep. 2011, 147(1):235-246.
Persico and Napolioni, "Autism genetics," Behav. Brain Res., Aug. 2013, 251:95-112.
Posey et al., "Developing drugs for core social and communication impairment in autism." Child Adolesc. Psychiatr. Clin. N. Am., Oct. 2008, 17(4):787-801.
Rabinowitz et al., "Negative symptoms in schizophrenia—the remarkable impact of inclusion definitions in clinical trials and their consequences," Schizophrenia Research, 2013, 150:334-338.
Reavill et al., "Pharmacological actions of a novel, high-affinity, and selective human dopamine D(3) receptor antagonist, SB-277011-A," J Pharmacol Exp Ther., 294(3):1154-1165, (Sep. 2000).
Rogóz et al., "Anxiolytic-like effect of nafadotride and PNU 99194A, dopamine D3 receptor antagonists in animal models," Pol J Pharmacol., 52(6)459-462, (2000).
Russell, "Neurobiology of animal models of attention-deficit hyperactivity disorder," J. Neurosci. Methods 161:185-198, (2007).
S. H. Kim, et al., "Preparation method of 4-biphenylacetic acid with high yield and high purity," Database WPI Week 200648, Thomson Scientific, London AN 206-468774, XP0-0258163, May 5, 2011.
Sachs, "Unmet clinical needs in bipolar disorder," J. Clin. Psychopharmacol., 2003, 23(3 Suppl 1):S2-S8.
Sautel et al., "Nafadotride, a potent preferential dopamine D3 receptor antagonist, activates locomotion in rodents," J. Pharmacol. Exp. Ther., 1995, 275:1239-1246.
Schneider and Przewlocki, "Behavioral alterations in rats prenatally exposed to valproic acid: animal model of autism," Neuropsychopharmacology, Jan. 2005, 30(1):80-89.
Schwartz et al., "Possible implications of the dopamine D(3) receptor in schizophrenia and in antipsychotic drug actions," Brain Res. Rev., Mar. 2000, 31(2-3):277-287.
Seeman, "Dopamine D2 receptors as treatment targets in schizophrenia," Clin Schizophr Relat Psychoses., 4(1):56-73, (Apr. 2010).
Seeman, "Antipsychotic drugs, dopamine receptors and schizophrenia," Clin. Neurosci. Res., 1:53-60, (2001).
Seeman, "Brain dopamine receptors" Pharmacological Reviews, 32(3): 229-313 (1980).
Shafer and Levant, "The D3 dopamine receptor in cellular and organismal function," Psychopharmacology (Berl), v, 135:1-16, (1998).
Shahid et al., "Asenapine: a novel psychopharmacologic agent with a unique human receptor signature," J. Psychopharmacol., Jan. 2009, 23(1):65-73.
Shalev et al., "Neurobiology of relapse to heroin and cocaine seeking: a review.," Pharmacol. Rev. 54 (1), 1-42, (2002).
Shapiro et al., "Aripiprazole, a novel atypical antipsychotic drug with a unique and robust pharmacology," Neuropsychopharmacology, Aug. 2003, 28(8):1400-1411.
Siegel and Rathbone, Chapter 2: Overview of Controlled Release Mechanisms, Fundamentals and Applications of Controlled Release Drug Delivery, 2011, Siepmann et al. eds., 25 pages.
Sigala et al., "Opposite effects of dopamine $D_2$ and $D_3$ receptors on learning and memory in the rat," Eur. J. Pharmacol., 336:107-112, (1997).
Smith et al., "Maximizing response to first-line antipsychotics in schizophrenia: a review focused on finding from meta-analysis," Psychopharmacology, Feb. 2019, 236(2):545-549.
Smith et al., "The dopamine D3/D2 receptor agonist 7-OH-DPAT induces cognitive impairment in the marmoset," Pharmacol. Biochem. Behav., 63:201-211, (1999).
Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).
Stahl and Grady, "A critical review of atypical antipsychotic utilization: comparing monotherapy with polypharmacy and augmentation," Curr. Med. Chem., 11:313-327, (2004).
Stahl, Essential Psychopharmacology: Neuroscientific Basis and Practical Applications, 2nd ed., p. 409, Cambridge University Press, pp. 409-414, (2000).
Steiner et al., "D3 dopamine receptor-deficient mouse: evidence for reduced anxiety," Physiol Behav., 63(1):137-141, print 1998, (1997).
Stemp et al., "Design and synthesis of trans-N-[4-[2-(6-cyano-l,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," J. Med. Chem., 43(9):1878-1885, (2000).
Szekely et al., "Genotoxic Impurities in Pharmaceutical Manufacturing: Sources, Regulations, and Mitigation," Chemical Review, Aug. 2012, 4 pages.
Tada et al., "Combined treatment of quetiapine with haloperidol in animal models of antipsychotic effect and extrapyramidal side effects: comparison with risperidone and chlorpromazine," Psychopharmacology, 2004, 176(1):94-100.
Tadori et al., "In vitro pharmacology of aripiprazole, its metabolite and experimental dopamine partial agonists at human dopamine D2 and D3 receptors," Eur. J. Pharmacol., Oct. 2011, 668(3):355-365.
Teng et al., "Reversal of social deficits by subchronic oxytocin in two autism mouse models," Neuropharmacology, Jun. 2016, 105:61-71.
Thanos et al., "The effects of two highly selective dopamine D3 receptor antagonists (SB-277011A and NGB-2904) on food self-administration in a rodent model of obesity," Pharmacol Biochem Behav. 89: 499-507, (2008).
Torisawa et al., "Progress in arylpiperazine synthesis by the catalytic amination reaction," Bioorganic and Medicinal Chemistry,Dec. 2002, 10(12):4023-4027.
Ukai et al., "Effects of the dopamine D3 receptor agonist, R(+)-7-hydroxy-N,N-di-n-propyl-2-aminotetralin, on memory processes in mice," Eur. J. Pharmacol., 1997, 324:147-151.
Ulrich, "Crystallization," Kirk-Othmer Encyclopedia of Chemical Technology, 2002, Chapter 4, 7 pages.
Vahia, "Diagnostic and statistical manual of mental disorders 5: A quick glance," Indian J. Psychiatry, Jul. 2013, 55(3):220-3.

(56) References Cited

OTHER PUBLICATIONS

Van der Kooij and Glennon, "Animal models concerning the role of dopamine in attention-deficit hyperactivity disorder," Neuroscience and Biobehavioral Reviews, 2007, 31: 597-618.
Vanderschuren and Trezza, "What the laboratory rat has taught us about social play behavior: role in behavioral development and neural mechanisms," Curr. Top Behav. Neurosci., 2013, 16:189-212.
Vippagunta et al., "Crystalline solids," Adv Drug Deliv Rev., 48(1):3-26, (May 16, 2001).
Waters et al., "Differential effects of dopamine D2 and D3 receptor antagonists in regard to dopamine release, in vivo receptor displacement and behavior," J. Neural. Transm. Gen. Sect., 98:39-55, (1994).
West, "Solid Solutions," Solid State Chemistry and Its Applications, Wiley, Chapter 10, pp. 358, pp. 365 (1988).
Willner et al., "Dopaminergic mechanism of antidepressant action in depressed patients," J. Affective Disorders 86: 37-45, (2005).
World Health Organization, The World Health Report 2001; Mental Health: New Understanding, New Hope, http://www.who.int/whr/2001/en/2001, 169 pages (2001).
Wustrow et al., "Aminopyrimidines with High Affinity for Both Serotonin and Dopamine Receptors," J. Med. Chem,, 1998, 41:760-771.
Wyatt and Henter, "An economic evaluation of manic-depressive illness—1991," Soc. Psychiatry Psychiatr. Epidemiol., 30(5):213-219, (1995).
Youdim, "The path from anti Parkinson drug selegiline and rasagiline to multifunctional neuroprotective anti Alzheimer drugs ladostigil and m30," Curr Alzheimer Res., 2006, 3(5):541-550.
Young et al., "A rating scale for mania: reliability, validity and sensitivity," The British Journal of Psychiatry, 1978, 133:429-435.
Zink et al., "Combination of amisulpride and olanzapine in treatment-resistant schizophrenic psychoses," Eur. Psychiatry, 2004, 19:56-58.
Abstracts of Papers, 234th ACS National Meeting, Boston, MA, United States, Aug. 19-23, 2007, MEOI-383, Abstracts published Jul. 25, 2007, 268 pages.
Laszlovsky et al., "Dopamine 02/03 Receptor Occupancy of RGH-188, a 03/02 Antagonist/Partial Agonist Antipsychotic, in Healthy Volunteers," 20th Congress of the European College of Neuropsychopharmacology, Vienna Austria, Oct. 13-17, 2007, 1 page.
Office Action in U.S. Appl. No. 12/504,149, dated Aug. 22, 2012, 8 pages.
Office Action in U.S. Appl. No. 12/504,149, dated Dec. 19, 2013, 9 pages.
Office Action in U.S. Appl. No. 12/504,149, dated Mar. 21, 2012, 7 pages.
Office Action in U.S. Appl. No. 13/653,576, dated Feb. 4, 2013, 5 pages.
Office Action in U.S. Appl. No. 13/653,576, dated Jun. 4, 2014, 8 pages.
Office Action in U.S. Appl. No. 13/653,576, dated May 28, 2013, 7 pages.
Office Action in U.S. Appl. No. 13/653,576, dated Nov. 6, 2013, 10 pages.
van Aerde et al. [International Journal of Pharmaceutics 45:145-152, 1988.
Keith, "Advances in psychotropic formulations," Prog Neuro-Psychopharmacol Biol Psychiatry., Aug. 30, 2006, 30(6):996-1008.
PCT International Search Report and Written Opinion in International Appln. No. PCT/US2009/50835, dated Sep. 10, 2009, 9 pages.
Preechagoon et al., "Improved Dissolution Rate of Poorly Soluble Drug by Incorporation of Buffers," Drug Development and Industrial Pharmacy., 2000, 26(8): 891-894.
International Preliminary Report on Patentability in International Application No. PCT/IB2013/060465, dated Jun. 11, 2015, 4 pages.
International Search Report and Written Opinion in International Application No. PCT/IB2013/060465, dated Jan. 22, 2014, 6 pages.
Laszlovsky et al., Dopamine D2/D3 Receptor Occupancy of RGH-188, a D3/D2 Antagonist/Partial Agonist Antipsychotic, in Healthy Volunteers, 20th Congress of the European College of Neuropsychopharmacology, Vienna Austria, Oct. 13-17, 2007.
Abstracts of Papers, 234th ACS National Meeting, Boston, MA, United States, Aug. 19-23, 2007, MEDI-383.
Non-Final Office Action mailed Mar. 21, 2012 in U.S. Appl. No. 12/504,149, filed Jul. 16, 2009 by Sarkar et al.
Final Office Action mailed Aug. 22, 2012 in U.S. Appl. No. 12/504,149, filed Jul. 16, 2009 by Sarkar et al.
International Search Report and Written Opinion for PCT/US2009/50835, mailed Sep. 10, 2009.
"The ICD-10 classification of mental and behavioural disorders : clinical descriptions and diagnostic guidelines," Geneva (1992): World Health Organization, 263 pages.
FDA guidelines, "Dissolution Testing of Immediate Release Solid Oral Dosage Forms", issued Aug. 1997, Section IV-A, 5 pages.
FDA guidelines, "Extended Release Oral Dosage Forms: Development, Evaluation and Application of In Vitro/In Vivo Correlation", Food and Drug Administration, CDER, Sep. 1997, p. 17.
FDA guidelines, "Q3B(R2) Impurities in New Drug Products," Revision 2, Jul. 2006, 18 pages.
Levant and McCarson, "D(3) dopamine receptors in rat spinal cord: implications for sensory and motor function," *Neurosci Lett*., 303(1):9-12, Apr. 27, 2001.
Levant et al., "Dopamine D3 Receptors," CNS Drugs, 12(5):391-402, Nov. 1999.
Levant, "The D3 dopamine receptor: neurobiology and potential clinical relevance," *Pharmacol Rev*., 49(3):231-252, Sep. 1997.
Pilla et al., "Selective inhibition of cocaine-seeking behaviour by a partial dopamine D3 receptor agonist," *Nature*, 400(6742):371-375, Jul. 22, 1999.
Schwartz et al., "Dopamine D3 receptor: basic and clinical aspects," *Clin Neuropharmacol*., 16(4):295-314, Aug. 1993.
Sokoloff et al., "Molecular cloning and characterization of a novel dopamine receptor (D3) as a target for neuroleptics," *Nature*., 347(6289):146-151, Sep. 13, 1990.
Wong and Van Tol, "Schizophrenia: from phenomenology to neurobiology," *Neurosci Biobehav Rev*., 27(3):269-306, May 2003.
Office Action in U.S. Appl. No. 12/504,149, mailed Dec. 19, 2013, 9 pages.

PHARMACEUTICAL FORMULATIONS CONTAINING DOPAMINE RECEPTOR LIGANDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

*More than one reissue application has been filed for the reissue of U.S. Pat. No. 9,056,846. The reissue application numbers are 16/384,264 (the present application) filed on Apr. 15, 2019 and 15/598,971 filed on May 18, 2017 (now U.S. Pat. No. RE47,350).*

This *is an* application *for reissue of U.S. Pat. No. 9,056,846, and is a continuation application of U.S. Ser. No. 15/598,971, filed May 18, 2017, which issued as U.S. Pat. No. RE47,350 on Apr. 16, 2019, and which is also a reissue application of U.S. application Ser. No. 13/653,576, filed Oct. 17, 2012, which issued as U.S. Pat. No. 9,056,846 on Jun. 16, 2015, and which* is a continuation of U.S. application Ser. No. 12/504,149 filed on Jul. 16, 2009*, which issued as U.S. Pat. No. 9,056,845 on Jun. 16, 2015,* and claims the benefit of U.S. Provisional Application No. 61/081,052, filed Jul. 16, 2008, all of which [is] *are* incorporated herein by reference.

FIELD OF THE INVENTION

The present invention relates to stable and bioavailable immediate release formulations comprising dopamine receptor ligands. Methods of treating various disorders by administering the formulations are also described.

BACKGROUND OF THE INVENTION

Solid oral drug compositions or preparations have various release profiles such as an immediate release profile as referenced by FDA guidelines ("Dissolution Testing of Immediate Release Solid Oral Dosage Forms", issued August/1997, Section IV-A) or an extended release profile as referenced by FDA Guidelines ("Extended Release Oral Dosage Forms: Development, Evaluation, and Application of In Vitro/InVivo Correlations", Food and Drug Administration, CDER, September 1997, Page 17). In the dissolution testing guideline for immediate release profiles, materials which dissolve at least 80% in the first 30 to 60 minutes in solution qualify as immediate release profiles. Therefore, immediate release solid dosage forms permit the release of most or all of the active ingredient over a short period of time, such as 60 minutes or less, and make rapid absorption of the drug possible.

Additional advantages of immediate release formulations include increased flexibility in drug administration by allowing the target drug to be administered either as multiples of lower strength formulations or as one higher strength formulation.

Food and Drug Administration guidelines (see, e.g., ICH Guideline Q3B, Revision 2, July 2006) provide limits for the amount of degradation product(s) that may be present in pharmaceutical formulations.

| Maximum Daily Dose | Degradation Product Threshold |
|---|---|
| <10 mg | 1.0% or 50 μg TDI, whichever is lower |
| 10 mg-100 mg | 0.5% or 200 μg TDI, whichever is lower |
| >100 mg-2 g | 0.2% or 3 mg TDI, whichever is lower |

TDI: Total daily intake

If the amount of degradation products exceeds the above thresholds, additional safety and toxicity studies may be required in accordance with the guidelines. To avoid the need for additional testing, it is therefore important to develop dosage forms that are stable over extended periods of time, and contain amounts of degradation product(s) within the FDA guidelines.

There is a need for stable dosage forms containing these compounds which comply with FDA degradation product guidelines. Applicants have now developed stable and bioavailable immediate release formulations containing (thio)-carbamoyl-cyclohexane derivatives. These formulations are disclosed herein.

SUMMARY OF THE INVENTION

In one embodiment, the present invention relates to (thio)-carbamoyl-cyclohexane derivatives, such as cariprazine (trans-1{4-[2-[4-(2,3-dichlorophenyl)-piperazin-1-yl]-ethyl]-cyclohexyl}-3,3-dimethyl-urea) and pharmaceutically acceptable salts thereof, e.g., cariprazine hydrochloride that can be formulated into immediate release dosage forms in which the dosage forms have advantageous stability profiles and wherein the dosage forms preferably release the drug rapidly and are bioavailable.

In another embodiment, stable and bioavailable formulations comprising cariprazine or pharmaceutically acceptable salts thereof are described in which the amount of hydrolysis degradation product is less than about 1% w/w.

In yet another embodiment, stable and bioavailable formulations comprising cariprazine hydrochloride are described in which the amount of hydrolysis degradation product is less than about 1% w/w.

In additional embodiments, formulations containing from about 0.05 mg to about 15 mg cariprazine or pharmaceutically acceptable salts thereof are described wherein a single dose administration of the formulation provides an in vivo plasma profile comprising (i) a mean $C_{max}$ of less than about 26.3 ng/mL, (ii) a mean $AUC_{0-\infty}$ of more than about 2 ng·hr/mL and (iii) a mean $T_{max}$ of about 3 or more hours.

In another embodiment, a pharmaceutical formulation is described comprising:

(a) between about 0.5% and about 15% of trans-1{4-[2-[4-(2,3-dichlorophenyl)-piperazin-1-yl]-ethyl]-cyclohexyl}-3,3-dimethyl-urea hydrochloride, (b) between about 5% and about 95% of lactose monohydrate, (c) between 0% and about 10% of talc, (d) between 0% and about 5% of colloidal silicon dioxide, (e) between 0% and about 15% of sodium starch glycolate, (f) between 0% and about 15% of hydroxypropyl cellulose, and (g) between about 0.1% and about 3% of magnesium stearate.

In yet another embodiment, a pharmaceutical formulation is described comprising:

(a) between about 0.5% and about 15% of trans-1{4-[2-[4-(2,3-dichlorophenyl)-piperazin-1-yl]-ethyl]-cyclohexyl}-3,3-dimethyl-urea hydrochloride, (b) between about 0.1% and about 20% of sodium carbonate, (c) between 0% and about 10% of talc, (d) between 0% and about 5% of colloidal silicon dioxide, (e) between 0% and about 15% of sodium starch glycolate, (f) between about 5% and about 95% of microcrystalline cellulose, and (g) between about 0.1% and about 3% of magnesium stearate.

In further embodiments, formulations comprising cariprazine hydrochloride are described in which the formulation releases the active ingredient at a rate of more than about 80% within about the first 60 minutes following administration of the formulation to a patient in need thereof.

In yet other embodiments, methods of treating conditions that require modulation of a dopamine receptor comprising administering to a patient in need thereof an effective amount of a formulation comprising cariprazine or pharmaceutically acceptable salts thereof are described in which the amount of hydrolysis degradation product is less than about 1% w/w.

DETAILED DESCRIPTION OF THE INVENTION

One embodiment of the present invention comprises trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the formulation comprises less than about 1% w/w trans-4-[2-[4-(2,3-dichlorophenyl)-piperazin-1-yl]-ethyl]-cyclohexyl-amine, or a pharmaceutically acceptable salt thereof. U.S. Patent Publication No. 2006/0229297 discloses (thio)-carbamoyl-cyclohexane derivatives as dopamine $D_3/D_2$ receptor antagonists. All derivatives cited in the U.S. Publication are hereby incorporated by reference in their entirety. One particular compound disclosed therein has structural formula (I):

(I)

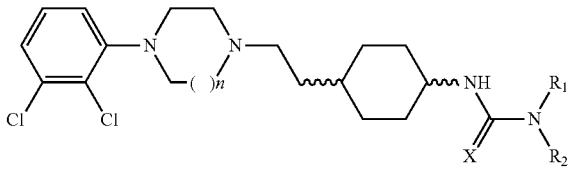

wherein $R_1$ and $R_2$ are each, independently, hydrogen, alkyl, alkenyl, aryl, cycloalkyl or aroyl, or $R_1$ and $R_2$ form a heterocyclic ring with the adjacent nitrogen atom;

X is O or S;

n is 1 or 2;

and/or geometric isomers and/or stereoisomers and/or diastereomers and/or salts and/or hydrates and/or solvates thereof.

Compounds of formula (I) are orally active and very potent dopamine $D_3/D_2$ receptor antagonists, which bind with significantly higher potency to $D_3$ than $D_2$ receptors.

The compounds of formula (I) have been found to be hydrolytically unstable. For example, trans-1{4-[2-[4-(2,3-dichlorophenyl)-piperazin-1-yl]-ethyl]-cyclohexyl}-3,3-dimethyl-urea hydrochloride (cariprazine hydrochloride) undergoes hydrolytic cleavage of the amide bond to form trans-4-[2-[4-(2,3-dichlorophenyl)-piperazin-1-yl]-ethyl]-cyclohexyl-amine dihydrochloride (De-BOC). Applicants have found that compounds of formula (I) undergo hydrolytic degradation when formulated with commonly used excipients (e.g., anhydrous dicalcium phosphate, microcrystalline cellulose containing 5% water). The formation of a degradation product such as De-BOC in a pharmaceutical formulation is detrimental to activity. Moreover, if the amount of degradation product exceeds FDA guidelines, additional safety and toxicology testing must be undertaken. Thus, it is important that stable and bioavailable formulations containing, for example, cariprazine and its salts, be developed, in which the amount of degradation product present falls within accepted FDA guidelines.

The preparation of stable and bioavailable dosage forms containing compounds of formula (I) is; however, not straightforward. For example, the use of low-moisture grade microcrystalline cellulose (e.g., Avicel PH 112), moisture absorbing/adsorbing agents (e.g., magnesium oxide) or chelating agents (e.g., ethylenediamaintetraacetic acid "EDTA") does not provide formulations with enhanced stability toward hydrolytic degradation product formation.

Applicants have surprisingly found that stable and bioavailable immediate release dosage forms comprising a compound of formula (I), or a pharmaceutically acceptable salt thereof (e.g., cariprazine hydrochloride) can be prepared. The formulations exhibit enhanced stability with respect to degradation product formation, are highly bioavailable and release the active ingredient in the stomach environment, e.g. at pH 1-4.

In one aspect, stable formulations of the present invention may be prepared by controlling the solid-state microenvironmental pH of the formulation. Thus, in one embodiment, the present invention relates to pharmaceutical formulations (e.g., solid oral dosage forms) comprising a compound of formula (I), or a pharmaceutically acceptable salt thereof, and a compound that modulates the pH environment of the solid formulation (e.g., an alkaline or acidic buffering agent). Suitable buffering agents include, for example, organic compounds (e.g., triethylamine, arginine, diethanolamine, and meglumine), carbonates (e.g., sodium carbonate, lithium carbonate, potassium carbonate, magnesium carbonate) and bicarbonates (e.g., sodium bicarbonate, lithium bicarbonate, potassium bicarbonate, magnesium bicarbonate). An exemplary formulation comprises a compound of formula (I), or a pharmaceutically acceptable salt thereof (e.g., cariprazine hydrochloride), and sodium carbonate. In certain embodiments, the amount of the buffering agent (e.g., sodium carbonate) is between about 0.1% and about 50% w/w, for example, between about 1% and about 15% w/w. Suitable ratios of the compound of formula (I), or a pharmaceutically acceptable salt thereof to the buffering agent are, e.g., from about 1.2 to about 12.8. In certain embodiments, the microenvironmental pH of the formulation is more than about 6, for example, more than about 8, more than about 9, more than about 10.

Without wishing to be bound by theory, Applicants believe that raising the solid state microenvironmental pH of the formulation enhances stability of the active agent toward degradation by reducing ionization of the weakly basic drug and thereby inhibiting hydrolysis.

In another aspect, stable formulations may be prepared by formulating a compound of formula (I), or a pharmaceutically acceptable salt thereof, with an excipient having a low water activity (i.e., an excipient that has a low amount of free water that may be released to effect hydrolytic degradation of the active ingredient). Applicants surprisingly found that the total amount of water present within an excipient is not the controlling factor regarding hydrolytic degradation. Rather, it is the amount of water present within an excipient that is available to be released that is the controlling factor in reducing hydrolytic degradation. For example, cariprazine hydrochloride formulations containing Avicel PH 102 (a microcrystalline cellulose containing about 5% water) in the absence of a buffering agent (e.g., sodium carbonate) show substantial formation of De-Boc after storage at 1 month at 40° C. and 75% Relative Humidity (RH). In contrast, cariprazine hydrochloride formulations containing lactose monohydrate with about 5% water show non-detectable levels of De-Boc after storage for 6 months under similar storage conditions.

Thus, in another embodiment, the present invention relates to pharmaceutical formulations (e.g., solid oral dosage forms) comprising a compound of formula (I), or a pharmaceutically acceptable salt thereof, and an excipient selected from lactose monohydrate, pregelatinized starch (e.g., Starch 1500), mannitol, and dicalcium phosphate dihydrate. An exemplary formulation comprises a compound of formula (I), or a pharmaceutically acceptable salt thereof (e.g. cariprazine hydrochloride), and lactose monohydrate. A further exemplary formulation comprises a compound of formula (I), or a pharmaceutically acceptable salt thereof and dicalcium phosphate dihydrate. A further exemplary formulation comprises a compound of formula (I), or a pharmaceutically acceptable salt thereof and mannitol.

In certain embodiments of the compound of formula (I), when $R_1$ and/or $R_2$ represent alkyl, the alkyl moiety is a substituted or unsubstituted saturated hydrocarbon radical which may be straight-chain or branched-chain and contains about 1 to about 6 carbon atoms (e.g., 1 to 4 carbon atoms), and is optionally substituted with one or more $C_{1-6}$ alkoxycarbonyl, aryl (e.g., phenyl) or ($C_{1-6}$ alkoxycarbonyl)-$C_{1-6}$ alkyl groups, or combinations thereof.

In additional embodiments, $R_1$ and $R_2$ form a heterocyclic ring with the adjacent nitrogen atom, which may be a saturated or unsaturated, optionally substituted, monocyclic or bicyclic ring, which may contain further heteroatoms selected from O, N, or S. For example, the heterocyclic ring can be pyrrolidine, piperazine, piperidine or morpholine.

In additional embodiments, when $R_1$ and/or $R_2$ represent alkenyl, the alkenyl moiety may have 2 to 7 carbon atoms and 1 to 3 double bonds.

In additional embodiments, when $R_1$ and/or $R_2$ represent aryl, the aryl moiety may be selected from an optionally substituted mono-, bi- or tricyclic aryl, such as, but not limited to, phenyl, naphthyl, fluorononyl, or anthraquinonyl group (e.g., phenyl or naphthyl). The aryl moiety may be substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen, cyano groups or combinations thereof.

In additional embodiments, when $R_1$ and/or $R_2$ represent cycloalkyl, the cycloalkyl moiety may be selected from an optionally substituted mono-, bi- or tricyclic cycloalkyl group, such as cyclohexyl or adamantyl.

In additional embodiments, when $R_1$ and/or $R_2$ represent aroyl the aryl moiety therein is as defined above, e.g., phenyl.

In exemplary embodiments, the compound of formula (I) is trans-1{4-[2-[4-(2,3-dichlorophenyl)-piperazin-1-yl]-ethyl]-cyclohexyl}-3,3-dimethyl-urea, or a pharmaceutically acceptable salt thereof, for example, trans-1{4-[2-[4-(2,3-dichlorophenyl)-piperazin-1-yl]-ethyl]-cyclohexyl}-3,3-dimethyl-urea hydrochloride In additional embodiments, the present invention relates to formulations comprising trans-1{4-[2-[4-(2,3-dichlorophenyl)-piperazin-1-yl]-ethyl]-cyclohexyl}-3,3-dimethyl-urea, or a pharmaceutically acceptable salt thereof in which the amount of De-BOC present is less than about 1% w/w, such as less than about 0.5% w/w. For example, in accordance with FDA guidelines, the amount of De-Boc present is less than 1% w/w (for dosage forms containing up to about 5 mg active agent), less than about 0.5% w/w (for dosage forms containing from about 5.1 mg to about 10 mg active agent), less than about 0.5% w/w (for dosage forms containing from about 10.1 mg to about 40 mg active agent).

Exemplary cariprazine hydrochloride formulations are set forth in Tables 1 and 2.

TABLE 1

Formulations Containing Lactose Monohydrate

| Ingredient | Function | Range (% w/w) | Preferred Range (% w/w) | 1st Exemplary Amount (% w/w) | 2nd Exemplary Amount (% w/w) |
|---|---|---|---|---|---|
| Lactose monohydrate | Filler | 5-95 | 75-95 | 89.0 | 85.9 |
| Cariprazine hydrochloride | Active | 0.5-15 | 0.8-4 | 0.8 | 3.9 |
| Talc USP | Glidant | 0-10 | 0-5 | 2.5 | 1.0 |
| Collodial silicon dioxide | Glidant | 0-5 | 0-2 | 1.0 | 2.5 |
| Sodium starch glycolate | Disintegrant | 0-15 | 2-8 | 4.0 | 4.0 |
| Hydroxypropyl cellulose | Binder | 0-15 | 2-8 | 2.0 | 2.0 |
| Magnesium stearate | Lubricant | 0.1-3.0 | 0.25-2.0 | 0.7 | 0.7 |
| Total (Core Tablets) | | 100.0 | 100.0 | 100.0 | 100.0 |
| Opadry Coating | Film | 1-10 | 2-5 | 3.0 | 3.0 |
| Total (Coated Tablets) | | | | 103.0 | 103.0 |

TABLE 2

Formulations Containing Sodium Carbonate

| Ingredient | Function | Range (% w/w) | Preferred Range (% w/w) | Exemplaty Amount (% w/w) |
|---|---|---|---|---|
| Microcrystalline cellulose (Avicel PH102) | Filler | 5-95 | 75-95 | 86.2 |
| Cariprazine hydrochloride | Active | 0.5-15 | 0.8-4 | 0.8 |
| Talc USP | Glidant | 0-10 | 0-5 | 3.0 |
| Collodial silicon dioxide | Glidant | 0-5 | 0-2 | 1.0 |
| Sodium starch glycolate | Disintegrant | 0-15 | 2-8 | 3.0 |
| Magnesium stearate | Binder | 0.1-3.0 | 0.25-2.0 | 1.0 |

TABLE 2-continued

| Formulations Containing Sodium Carbonate | | | | |
|---|---|---|---|---|
| Ingredient | Function | Range (% w/w) | Preferred Range (% w/w) | Exemplaty Amount (% w/w) |
| Sodium carbonate | pH Modifier | 0.1-20 | 5-10 | 5.0 |
| Total (Core Tablets) | | 100.0 | 100.0 | 100.0 |
| Opadry | Film Coating | 1-10 | 3.0 | 3.0 |
| Total (Coated Tablets) | | | 103.0 | 103.0 |

The plasma concentration of the immediate release formulations of the present invention have a time of maximum plasma concentration ($T_{max}$) in human patients ranging from between about 3 to about 6 hours, and an in vitro release rate of more than about 80% in about 60 minutes, more preferably in about 30 minutes.

The pharmaceutical formulations of the present invention allow for modification of the $C_{max}$ by changing the strength of the formulation without substantially affecting the $T_{max}$, of the drug. The immediate release formulations described in the present invention provide the desired $T_{max}$ without compromising the initial peak ($C_{max}$).

In a further aspect, the present invention relates to a formulation comprising from about 0.05 mg to about 15 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 26.3 ng/mL, (ii) a mean $AUC_{0-\infty}$ of more than about 2 ng·hr/mL and (iii) a mean $T_{max}$ of about 3 or more hours. For example, the formulation provides an in vivo plasma profile comprising (i) a mean $C_{max}$ of less than about 22.5 ng/mL, (ii) a mean $AUC_{0-\infty}$ of more than about 3 ng·hr/mL and (iii) a mean $T_{max}$ of about 3 or more hours.

In one embodiment, the formulation comprises about 0.1 mg trans-1{4-[2-[4-(2,3-dichlorophenyl)-piperazin-1-yl]-ethyl]cyclohexyl}-3,3-dimethyl-urea, or a pharmaceutically acceptable salt thereof, wherein the single dose administration of formulation provides an in vivo plasma profile comprising (i) a mean $C_{max}$ of less than about 0.2 ng/mL, (ii) a mean $AUC_{0-\infty}$ of more than about 2 ng·hr/mL and (iii) a mean $T_{max}$ of about 3 or more hours. For example, the formulation provides an in vivo plasma profile comprising (i) a mean $C_{max}$ of less than about 0.2 ng/mL, (ii) a mean $AUC_{0-\infty}$ of more than about 3 ng·hr/mL and (iii) a mean $T_{max}$ of about 3 or more hours.

In one embodiment, the formulation comprises about 0.25 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 0.5 ng/mL, (ii) a mean $AUC_{0-\infty}$ of more than about 5 ng·hr/mL and (iii) a mean $T_{max}$ of about 3 or more hours. For example, the formulation provides an in vivo plasma profile comprising (i) a mean $C_{max}$ of less than about 0.4 ng/mL, (ii) a mean $AUC_{0-\infty}$ of more than about 7 ng·hr/mL and (iii) a mean $T_{max}$ of about 3 or more hours.

In one embodiment, the formulation comprises about 0.5 mg trans-1{4-[2-[4-(2,3-dichlorophenyl)-piperazin-1-yl]ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 0.9 ng/mL, (ii) a mean $AUC_{0-\infty}$ of more than about 10 ng·hr/mL and (iii) a mean $T_{max}$ of about 3 or more hours. For example, the formulation provides an in vivo plasma profile comprising (i) a mean $C_{max}$ of less than about 0.8 ng/mL, (ii) a mean $AUC_{0-\infty}$ of more than about 15 ng·hr/mL and (iii) a mean $T_{max}$ of about 3 or more hours.

In one embodiment, the formulation comprises about 1 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 1.8 ng/mL, (ii) a mean $AUC_{0-\infty}$ of more than about 20 ng·hr/mL and (iii) a mean $T_{max}$ of about 3 or more hours. For example, the formulation provides an in vivo plasma profile comprising (i) a mean $C_{max}$ of less than about 1.5 ng/mL, (ii) a mean $AUC_{0-\infty}$ of more than about 30 ng·hr/mL and (iii) a mean $T_{max}$ of about 3 or more hours.

In one embodiment, the formulation comprises about 1.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 2.7 ng/mL, (ii) a mean $AUC_{0-\infty}$ of more than about 30 ng·hr/mL and (iii) a mean $T_{max}$ of about 3 or more hours. For example, the formulation provides an in vivo plasma profile comprising (i) a mean $C_{max}$ of less than about 2.3 ng/mL, (ii) a mean $AUC_{0-\infty}$ of more than about 45 ng·hr/mL and (iii) a mean $T_{max}$ of about 3 or more hours.

In one embodiment, the formulation comprises about 2 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 3.5 ng/mL, (ii) a mean $AUC_{0-\infty}$ of more than about 40 ng·hr/mL and (iii) a mean $T_{max}$ of about 3 or more hours. For example, the formulation provides an in vivo plasma profile comprising (i) a mean $C_{max}$ of less than about 3.0 ng/mL, (ii) a mean $AUC_{0-\infty}$ of more than about 60 ng·hr/mL and (iii) a mean $T_{max}$ of about 3 or more hours.

In one embodiment, the formulation comprises about 2.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 4.4 ng/mL, (ii) a mean $AUC_{0-\infty}$ of more than about 50 ng·hr/mL and (iii) a mean $T_{max}$ of about 3 or more hours. For example, the formulation provides an in vivo plasma profile comprising (i) a mean $C_{max}$ of less than about 3.8 ng/mL, (ii) a mean $AUC_{0-\infty}$ of more than about 75 ng·hr/mL and (iii) a mean $T_{max}$ of about 3 or more hours.

In one embodiment, the formulation comprises about 3 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 5.3 ng/mL, (ii) a mean $AUC_{0-\infty}$ of more than about 60 ng·hr/mL and (iii) a mean $T_{max}$ of about 3 or more hours. For example, the formulation provides an in vivo plasma profile comprising (i) a mean $C_{max}$ of less than about 4.5 ng/mL, (ii) a mean $AUC_{0-\infty}$ of more than about 90 ng·hr/mL and (iii) a mean $T_{max}$ of about 3 or more hours.

In one embodiment, the formulation comprises about 4.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 7.9 ng/mL, (ii) a mean $AUC_{0-\infty}$ of more than about 90 ng·hr/mL and (iii) a mean $T_{max}$ of about 3 or more hours. For example, the formulation provides an in vivo plasma profile comprising (i) a mean $C_{max}$ of less than about 6.8 ng/mL, (ii) a mean $AUC_{0-\infty}$ of more than about 135 ng·hr/mL and (iii) a mean $T_{max}$ of about 3 or more hours.

In one embodiment, the formulation comprises about 5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 8.8 ng/mL, (ii) a mean $AUC_{0-\infty}$ of more than about 100 ng·hr/mL and (iii) a mean $T_{max}$ of about 3 or more hours. For example, the formulation provides an in vivo plasma profile comprising (i) a mean $C_{max}$ of less than about 7.5 ng/mL, (ii) a mean $AUC_{0-\infty}$ of more than about 150 ng·hr/mL and (iii) a mean $T_{max}$ of about 3 or more hours.

In one embodiment, the formulation comprises about 6 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 10.5 ng/mL, (ii) a mean $AUC_{0-\infty}$ of more than about 120 ng·hr/mL and (iii) a mean $T_{max}$ of about 3 or more hours. For example, the formulation provides an in vivo plasma profile comprising (i) a mean $C_{max}$ of less than about 9.0 ng/mL, (ii) a mean $AUC_{0-\infty}$ of more than about 180 ng·hr/mL and (iii) a mean $T_{max}$ of about 3 or more hours.

In one embodiment, the formulation comprises about 7.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 13.2 ng/mL, (ii) a mean $AUC_{0-\infty}$ of more than about 150 ng·hr/mL and (iii) a mean $T_{max}$ of about 3 or more hours. For example, the formulation provides an in vivo plasma profile comprising (i) a mean $C_{max}$ of less than about 11.3 ng/mL, (ii) a mean $AUC_{0-\infty}$ of more than about 225 ng·hr/mL and (iii) a mean $T_{max}$ of about 3 or more hours.

In one embodiment, the formulation comprises about 9 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 15.8 ng/mL, (ii) a mean $AUC_{0-\infty}$ of more than about 180 ng·hr/mL and (iii) a mean $T_{max}$ of about 3 or more hours. For example, the formulation provides an in vivo plasma profile comprising (i) a mean $C_{max}$ of less than about 13.5 ng/mL, (ii) a mean $AUC_{0-\infty}$ of more than about 270 ng·hr/mL and (iii) a mean $T_{ma}$ of about 3 or more hours.

In one embodiment, the formulation comprises about 12.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 21.9 ng/mL, (ii) a mean $AUC_{0-\infty}$ of more than about 250 ng·hr/mL and (iii) a mean $T_{max}$ of about 3 or more hours. For example, the formulation provides an in vivo plasma profile comprising (i) a mean $C_{max}$ of less than about 18.8 ng/mL, (ii) a mean $AUC_{0-\infty}$ of more than about 375 ng·hr/mL and (iii) a mean $T_{max}$ of about 3 or more hours.

In one embodiment, the formulation comprises about 15 mg trans-1{4-[2-[4-(2,3-dichlorophenyl)-piperazin-1-yl]-ethyl]-cyclohexyl}-3,3-dimethyl-urea, or a pharmaceutically acceptable salt thereof, wherein the single dose administration of formulation provides an in vivo plasma profile comprising (i) a mean $C_{max}$ of less than about 26.3 ng/mL, (ii) a mean $AUC_{0-\infty}$ of more than about 300 ng·hr/mL and (iii) a mean $T_{max}$ of about 3 or more hours. For example, the formulation provides an in vivo plasma profile comprising (i) a mean $C_{max}$ of less than about 22.5 ng/mL, (ii) a mean $AUC_{0-\infty}$ of more than about 450 ng·hr/mL and (iii) a mean $T_{max}$ of about 3 or more hours.

Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride salt, a hydrobromide salt or a mesylate salt. In one embodiment, the pharmaceutically acceptable salt is a hydrochloride salt.

In another embodiment, the formulations of the present invention contain trans-1{4-[2-[4-(2,3-dichlorophenyl)-piperazin-1-yl]-ethyl]-cyclohexyl}-3,3-dimethyl-urea hydrochloride.

In yet another embodiment, the present invention relates to a formulation comprising from about 0.05 mg to about 15 mg trans-1{4-[2-[4-(2,3-dichlorophenyl)-piperazin-1-yl]-ethyl]-cyclohexyl}-3,3-dimethyl-urea hydrochloride, about 0.1 mg, about 0.25 mg, about 0.5 mg, about 1 mg, about 1.5 mg, about 2 mg, about 2.5 mg, about 3 mg, about 4.5 mg, about 5 mg, about 6 mg, about 7.5 mg, about 9 mg, about 12.5 mg, or about 15 mg. In other embodiments, the formulation is administered in an amount which ranges between any two of the dosage amounts.

In yet another embodiment, the present invention relates to a formulation comprising from about 0.05 mg to about 15 mg trans-1{4-[2-[4-(2,3-dichlorophenyl)-piperazin-1-yl]-ethyl]-cyclohexyl}-3,3-dimethyl-urea hydrochloride wherein the single dose administration of the formulation provides an in vivo plasma profile comprising (i) a mean $C_{max}$ of less than about 26.3 ng/mL, (ii) a mean $AUC_{0-\infty}$ of more than about 2 ng·hr/mL and (iii) a mean $T_{max}$ of about 3 or more hours. For example, the formulation provides an in vivo plasma profile comprising (i) a mean $C_{max}$ of less than about 22.5 ng/mL, (ii) a mean $AUC_{0-\infty}$ of more than about 3 ng·hr/mL and (iii) a mean $T_{max}$ of about 3 or more hours.

Some of the compounds useful in the formulations described herein may exist in different polymorphic forms. As known in the art, polymorphism is an ability of a compound to crystallize as more than one distinct crystalline or "polymorphic" species. The use of such polymorphs is within the scope of the present invention.

Some of the compounds useful in the formulations described herein may exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates. The use of such solvates is within the scope of the present invention.

Dosage Forms

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage forms is closely related to the therapeutic amounts of the compounds or formulations which are desirable and efficacious for the given treatment application.

Suitable dosage forms include, but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. Formulations suitable for oral administration are preferred (e.g., tablets, capsules).

To prepare such pharmaceutical dosage forms, the active ingredient, is typically mixed with a pharmaceutical carrier according to conventional pharmaceutical compounding techniques. The carrier may take a wide variety of forms depending on the form of preparation desired for administration.

In preparing the formulations in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Suitable carriesrs and additives include, for example, sucrose, mannitol, polyethylene glycol, hydroxypropyl cellulose, hydroxypropyl methyl cellulose, sodium lauryl sulphate, chremophor, tweens, spans, pluronics, microcrystalline cellulose, calcium phosphate, talc, fumed silica, hydroxypropyl methyl cellulose, wax, and fatty acids, etc.

Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each comprising a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

Dosages

The active ingredient present in the formulation can normally be administered in a combined daily dosage regimen (for an adult patient) of, for example, between about 0.05 mg and about 50 mg, between about 0.1 mg and about 20 mg, between about 0.1 mg and about 15 mg, between about 0.1 mg and about 12.5 mg.

In certain embodiments, the pharmaceutical formulation includes about 0.05 mg, about 0.1 mg, about 0.2 mg, about 0.25 mg, about 0.3 mg, about 0.4 mg, about 0.5 mg, about 0.75 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12.0 mg, about 12.5 mg, about 13.0 mg, about 13.5 mg, about 14.0 mg, about 14.5 mg or about 15.0 mg of active ingredient, such as trans-1{4-[2-[4-(2,3-dichlorophenyl)-piperazin-1-yl]-ethyl]-cyclohexyl}-3,3-dimethyl-urea, or pharmaceutically acceptable salt thereof (e.g., trans-1{4-[2-[4-(2,3-dichlorophenyl)-piperazin-1-yl]-ethyl]-cyclohexyl}-3,3-dimethyl-urea hydrochloride).

For example, the pharmaceutical formulation includes about 0.1 mg, about 0.25 mg, about 0.5 mg, about 1 mg, about 1.5 mg, about 2 mg, about 2.5 mg, about 3 mg, about 5 mg, about 6 mg, about 7.5 mg, about 9 mg, about 12.5 mg or about 15.0 mg of active ingredient, such as trans-1{4-[2-[4-(2,3-dichlorophenyl)-piperazin-1-yl]-ethyl]-cyclohexyl}-3,3-dimethyl-urea, or pharmaceutically acceptable salt thereof (e.g., trans-1{4-[2-[4-(2,3-dichlorophenyl)-piperazin-1-yl]-ethyl]-cyclohexyl}-3,3-dimethyl-urea hydrochloride).

In yet further embodiments, the active ingredient (e.g., trans-1{4-[2-[4-(2,3-dichlorophenyl)-piperazin-1-yl]-ethyl]-cyclohexyl}-3,3-dimethyl-urea, or a pharmaceutically acceptable salt thereof), is present in the formulation in an amount which ranges between any two of these dosage amounts (e.g., between about 0.1 mg and about 15 mg, between about 0.5 mg and about 12.5 mg, between about 1.5 mg and about 6 mg, between about 6 mg and about 12.5 mg).

The desired dose may be administered as one or more daily sub dose(s) administered at appropriate time intervals throughout the day, or alternatively, in a single dose, for example, for morning or evening administration. For example, the daily dosage may be divided into one, into two, into three, or into four divided daily doses.

The duration of the treatment may be decades, years, months, weeks, or days, as long as the benefits persist.

Methods of Treatment

The present invention further provides methods for treating conditions that requires modulation of a dopamine receptor, particularly, a dopamine $D_3$ and/or $D_2$ receptor. In further embodiments, the present invention provides methods for treating a condition that requires modulation of a dopamine D3 and/or $D_2$ receptor utilizing one or more formulations of the present invention.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions and addiction (see, e.g., Sokoloff, P. et al.: Nature, 1990, 347, 146; Schwartz, J. C., et al.: Clin. Neuropharmacol. 1993, 16, 295; Levant, B.: Pharmacol. Rev. 1997, 49, 231), addiction (see, e.g., Pilla, C. et al.: Nature 1999, 400, 371) and Parkinson's disease (see, e.g., Levant, B. et al.: CNS Drugs 1999, 12, 391) or pain (see, e.g., Levant, B. et al.: Neurosci. Lett. 2001, 303, 9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation or cognitive disturbances. These side effects seriously restrict the therapeutic utilization of $D_2$ antagonist compounds. (Wong A. H. C. et al., Neurosci. Biobehav. Rev., 27, 269, 2003)

In a further aspect, the present invention provides methods for treating conditions which require preferential modulation of dopamine $D_3$ and/or $D_2$ receptors, for example psychoses (e.g. schizophrenia, schizo-affective disorders), cognitive impairment accompanying schizophrenia, mild-to-moderate cognitive deficits, dementia, psychotic states associated with dementia, psychotic depression, mania, acute mania, paranoid and delusional disorders, dyskinetic disorders such as Parkinson's disease, neuroleptic induced parkinsonism, tardive dyskinesia, eating disorders (e.g. bulimia nervosa), attention deficit disorders, hyperactivity disorders in children, depression, anxiety, sexual dysfunction, sleep disorders, emesis, aggression, autism and drug abuse, which comprises administering to a subject in need thereof an effective amount of a compound and/or formulation of the present invention.

A preferred use for $D_3/D_2$ antagonists with $D_3$ preference according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, paranoid and delusional disorders, dyskinetic disorders such as Parkinson's disease, neuroleptic induced parkinsonism, depression, anxiety, drug abuse (e.g. cocaine abuse).

The particular combination of the two receptor-actions described above allows the simultaneous manifestation of the beneficial actions of both the $D_3$ antagonism (e.g. cognitive enhancer effect, inhibition of extrapyramidal motor symptoms, inhibitory action on drug abuse) and the $D_2$ antagonism (e.g. antipsychotic effect). Furthermore, the same combination surprisingly results in canceling out the disadvantageous features of $D_2$ antagonism (e.g. extrapyramidal symptoms, psychomotor sedation, cognitive disturbances).

In exemplary embodiments, the present invention relates to methods of treating schizophrenia (e.g., positive symptoms of schizophrenia, negative symptoms of schizophrenia). In another embodiment, the present invention relates to methods of treating cognitive defects associated with schizophrenia.

In another embodiment, the present invention relates to methods of treating acute mania.

In yet another embodiment, the present invention relates to methods of treating bipolar disorder.

DEFINITIONS

The term "pharmaceutically acceptable" means biologically or pharmacologically compatible for in vivo use in animals or humans, and preferably means approved by a regulatory agency of the Federal or a state government or listed in the U.S. Pharmacopeia or other generally recognized pharmacopeia for use in animals, and more particularly in humans.

The term "schizophrenia" is intended to include the group of mental disorders characterized by disruptions in thinking and perception, and includes schizophrenia (and all its subtypes; paranoid, catatonic, disorganized, residual, undifferentiated) and other psychotic disorders (as per Diagnostic and Statistical Manual for Mental Disorders, Fourth Edition, Washington, D.C. (1994): American Psychiatric Association, or The ICD-10 Classification of Mental and Behavioural Disorders: Clinical Descriptions and Diagnostic Guidelines, Geneva (1992): World Health Organization) such as schizophreniform and schizoaffective disorders, brief psychotic disorder, etc.

In a clinical evaluation, schizophrenia is commonly marked by "positive symptoms" such as hallucinations (especially auditory hallucination which are usually experienced as voices), disorganized thought processes and delusions as well as "negative symptoms" which include affective flattening, alogia, avolition, and anhedonia.

The term "the negative symptoms of schizophrenia" refer to a class of symptoms of schizophrenia which can be considered to reflect a 'loss' in functional, directed thought or activity. Negative symptoms of schizophrenia are well known in the art, and include affective flattening (characterized by, for example, an immobile and/or unresponsive facial expression, poor eye contact and reduced body language), alogia ('poverty of speech' or brief, laconic and/or empty replies), avolition (characterized by a reduced or absent ability to initiate and carry out goal-directed activities), anhedonia (loss of interest or pleasure), asocialty (reduced social drive and interaction), apathy and other negative symptoms known to those of skill in the art. The negative symptoms of schizophrenia may be assessed using any methodology known in the art including, but not limited to, the Brief Psychiatric Rating Scale (BPRS), and the Positive and Negative Symptom Scale (PANSS). The BPRS and PANSS have subscales or factors that can be used to measure negative symptoms. Other scales have been designed to address specifically negative symptoms: For example the Scale for the Assessment of Negative Symptoms (SANS), the Negative Symptoms Assessment (NSA) and the Schedule for the Deficit Syndrome (SDS). Subscales of the BPRS and PANSS may also be used to assess positive symptoms, although methods for specifically assessing positive symptoms are also available (e.g., the Scale for the Assessment of Positive Symptoms, or SAPS).

The terms "cognitive impairment associated with schizophrenia" and "cognitive defects associated with schizophrenia" refers to cognitive deficits in schizophrenia patients. Cognitive impairment in schizophrenia is a core feature of the illness (i.e. not a result of treatment or clinical symptoms). Cognitive deficits include, but are not limited to deficits of attention/vigilance, working memory, verbal learning and memory, visuospatial memory, reasoning/problem solving and social cognition. There are numerous neuropsychological tests used to measure cognitive deficits in schizophrenia, such as the Wisconsin Card Sorting Test (WCST).

The terms "treat," "treatment," and "treating" refer to one or more of the following: relieving or alleviating at least one symptom of a disorder in a subject; relieving or alleviating the intensity and/or duration of a manifestation of a disorder experienced by a subject; and arresting, delaying the onset (i.e., the period prior to clinical manifestation of a disorder) and/or reducing the risk of developing or worsening a disorder.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired activity upon administration to a mammal in need thereof. As used herein with respect to the pharmaceutical formulations comprising trans-1{4-[2-[4-(2,3-dichlorophenyl)-piperazin-1-yl]-ethyl]-cyclohexyl}-3,3-dimethyl-urea, or a pharmaceutically acceptable salt thereof, e.g., trans-1{4-[2-[4-(2,3-dichlorophenyl)-piperazin-1-yl]-ethyl]-cyclohexyl}-3,3-dimethyl-urea hydrochloride, the term "therapeutically effective amount/dose" refers to the amount/dose of the compound that, when combined, is sufficient to produce an effective response upon administration to a mammal.

A subject or patient in whom administration of the therapeutic compound is an effective therapeutic regimen for a disease or disorder is preferably a human, but can be any animal, including a laboratory animal in the context of a trial or screening or activity experiment. Thus, as can be readily appreciated by one of ordinary skill in the art, the methods, compounds and formulations of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean plus or minus a range of up to 20%, preferably up to 10%, more preferably up to 5%.

The pharmacokinetic parameters described herein include area under the plasma concentration-time curve ($AUC_{0-t}$ and $AUC_{0-\infty}$), maximum plasma concentration ($C_{max}$), time of maximum plasma concentration ($T_{max}$) and terminal elimination half-life ($T_{1/2}$). The time of maximum concentration, $T_{max}$, is determined as the time corresponding to $C_{max}$. Area under the plasma concentration-time curve up to the time corresponding to the last measurable concentration ($AUC_{0-t}$) is calculated by numerical integration using the linear trapezoidal rule as follows:

$$AUC_{0-t} = \sum_{i=2}^{n} 0.5 \cdot (C_i + C_{i-1}) \cdot (t_i - t_{i-1}) \quad \text{Eq. 1}$$

where $C_i$ is the plasma memantine concentrations at the corresponding sampling time point $t_i$ and n is the number of time points up to and including the last quantifiable concentration.

The terminal half-life ($T_{1/2}$) is calculated using the following equation:

$$T_{1/2} = \frac{0.693}{\lambda_z} \quad \text{Eq. 2}$$

where $\lambda_z$ is the terminal elimination rate constant.

The area under the plasma concentration-time curve from time zero to infinity is calculated according to the following equation:

$$AUC_{0-\infty} = AUC_{0-t} + \frac{C_{last}}{\lambda_z} \quad \text{Eq. 3}$$

where $C_{last}$ is the last measurable concentration.

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Avicel PH102 is a microcrystalline cellulose that may be obtained from FMC Biopolymer (Philadelphia, Pa.). Avicel PH 112 is a low moisture microcrystalline cellulose that may be obtained from FMC Biopolymer (Philadelphia, Pa.). Aerosil 200VV is a fumed silica that may be obtained from Evonik Industries/Degussa (Parsippany, N.J.). Prosolv SMC C90 is a microcrystalline cellulose that may be obtained from JRS Pharma (Paterson, N.Y.). Starch 1500 and Starcap 1500 are co-processed starches that may be obtained from Colorcon (West Point, Pa.). Starlac (a mixture of 85% lactose monohydrate and 15% maize starch) may be obtained from Roquette Pharma (Keokuk, Iowa). Syloid 63FP is a silica gel that may be obtained from Davison Chemical Division of W. R. Grace & Co. (Baltimore, Md.).

Dissolution rates were measured using a USP Apparatus II (paddle) with 500 ml of 0.01N HCl containing 0.25% polysorbate 80.

Example 1

Preparation of a Capsule Formulations Containing Cariprazine Hydrochloride

Example 1A

Capsules containing cariprazine hydrochloride and anhydrous calcium hydrogen phosphate were prepared according to Table 3.

TABLE 3

Composition of Capsule Formulations

| | Amount (% w/w) | | |
|---|---|---|---|
| Ingredient | Capsule I (0.5 mg)* | Capsule II (2.5 mg)* | Capsule III (12.5 mg)* |
| Cariprazine hydrochloride | 0.5 | 2.7 | 13.6 |
| Microcrystalline cellulose | 59.5 | 58.2 | 51.7 |
| Calcium hydrogen phosphate, anhydrous | 40.0 | 39.1 | 34.7 |
| Total | 100.0 | 100.0 | 100.0 |

*amount of cariprazine free base

The microcrystalline cellulose (Avicel PH 102) and anhydrous calcium hydrogen phosphate were sieved together through a sieve of 0.80 mm. The final powder was blended for 2 minutes in a high-shear mixer. The empty capsule shells were filled with the powder mixture using a manual capsule filling machine. The bulk filled capsules were then manually packaged into glass vials.

The stability of the capsule formulations (at 40° C. and 75% RH) is shown in Table 4.

TABLE 4

Formulation Stability

| | Amount of De-BOC (% w/w) | | |
|---|---|---|---|
| Time | Capsule I | Capsule II | Capsule III |
| Initial | <0.02 | <0.02 | <0.02 |
| 1 Month | 0.089 | <0.02 | <0.02 |
| 2 Months | 0.160 | 0.064 | <0.02 |
| 3 Months | 0.199 | 0.076 | <0.02 |
| 6 Months | Not Determined | 0.100 | <0.02 |

High levels of an additional degradation product were observed at 3 months for Capsule I.

Example 1B

Capsules containing cariprazine hydrochloride and pregelatinized starch were prepared according to Table 5:

TABLE 5

Composition of Capsule Formulations

| Ingredient | Amount (% w/w) Capsule I (0.5 mg)* | Capsule II (1.5 mg)* | Capsule III (6.0 mg)* |
|---|---|---|---|
| Cariprazine hydrochloride | 0.545 | 1.635 | 6.54 |
| Pregelatinized Starch | 98.455 | 97.365 | 92.46 |
| Magnesium stearate | 1.000 | 1.000 | 1.000 |
| Total | 100.0 | 100.0 | 100.0 |

*amount of cariprazine free base

The pregelatinized starch and cariprazine were sieved through a #20 sieve and mixed in a V-shell blender for 20 minutes by 5 step geometric mixing using an Intensifier bar in the final step. The magnesium stearate was sieved through #20 screen, added and the blend mixed for further 2 minutes. The final blend was then filled into capsules using a MG2 Futura Encapsulation machine. The capsules were packed into HDPE bottles and induction sealed.

The stability of the capsule formulations (at 40° C. and 75% RH) in a HDPE bottle, induction sealed with no dessicant is shown in Table 6.

TABLE 6

Formulation Stability

| Time | Amount of De-BOC (% w/w ) Capsule I | Capsule II | Capsule III |
|---|---|---|---|
| Initial | Not Detected | Not Detected | Not Detected |
| 1 Month | Not Detected | Not Detected | Not Detected |
| 2 Months | 0.061 | 0.070 | Not Detected |
| 3 Months | 0.093 | 0.075 | Not Detected |
| 6 Months | 0.159 | 0.106 | Not Detected |

Not detected means <0.05% w/w or below the limit of quantitation.

The dissolution rates for Capsules II and III is shown in Table 7.

TABLE 7

Dissolution Rates

| Time (mins) | % Dissolved Capsule II | Capsule III |
|---|---|---|
| 0 | 0 | 0 |
| 15 | 97 | 97 |
| 20 | 97 | 98 |
| 45 | 95 | 99 |
| 60 | 97 | 99 |

Example 1C

Capsules containing cariprazine hydrochloride, Starlac (a combination of 85% lactose monohydrate and 15% starch) were prepared according to Table 8.

TABLE 8

Composition of Capsule Formulation

| Ingredient | Amount (% w/w) Capsule I (0.5 mg)* |
|---|---|
| Cariprazine hydrochloride | 0.545 |
| Lactose monohydrate, starch (Starlac) | 98.455 |
| Magnesium stearate | 1.000 |
| Total | 100.0 |

*amount of cariprazine free base

The Starlac and cariprazine were sieved through a #20 sieve and mixed in a V-shell blender for 20 minutes by 5 step geometric mixing using an Intensifier bar in the final step. The magnesium stearate was sieved through #20 screen, added and the blend mixed for further 2 minutes. The final blend was then filled into capsules using a MG2 Futura Encapsulation machine. The capsules were packed into HDPE bottles and induction sealed.

The stability of the capsule formulations (at 40° C. and 75% RH)) in a HDPE bottle, induction sealed with no dessicant is shown in Table 9.

TABLE 9

Formulation Stability

| Time | Amount of De-BOC (% w/w ) Capsule I |
|---|---|
| Initial | Not Detected |
| 2 weeks | Not Detected |
| 1 Month | Not Detected |
| 2 Months | Not Detected |
| 3 Months | Not Detected |

Example 1D

Capsules containing cariprazine hydrochloride and mannitol were prepared according to Table 10:

TABLE 10

Composition of Capsule Formulation

| Ingredient | Amount (% w/w) Capsule 1(0.5 mg)* |
|---|---|
| Cariprazine hydrochloride | 0.545 |
| Mannitol | 98.455 |
| Magnesium stearate | 1.000 |
| Total | 100.0 |

*amount of cariprazine free base

The mannitol and cariprazine were sieved through a #20 sieve and mixed in a V-shell blender for 20 minutes by 5 step geometric mixing using an Intensifier bar in the final step. The magnesium stearate was sieved through #20 screen, added and the blend mixed for further 2 minutes. The final blend was then filled into capsules using a MG2 Futura Encapsulation machine. The capsules were packed into HDPE bottles and induction sealed.

The stability of the capsule formulations (at 40° C. and 75% RH) in a HDPE bottle, induction sealed with no dessicant is shown in Table 11.

TABLE 11

Formulation Stability

| Time | Amount of De-BOC (% w/w) Capsule I |
|---|---|
| Initial | Not Detected |
| 2 weeks | Not Detected |
| 1 Month | Not Detected |
| 2 Months | Not Detected |
| 3 Months | 0.105 |

Example 1E

Capsules containing cariprazine hydrochloride and lactose monohydrate were prepared according to Table 12:

TABLE 12

Composition of Capsule Formulation

| Ingredient | Amount (% w/w) Capsule I (0.5 mg)* |
|---|---|
| Cariprazine hydrochloride | 0.545 |
| Lactose monohydrate | 98.455 |
| Magnesium stearate | 1.000 |
| Total | 100.0 |

*amount of cariprazine free base

The lactose monohydrate and cariprazine were sieved through a #20 sieve and mixed in a V-shell blender for 20 minutes by 5 step geometric mixing using an Intensifier bar in the final step. The magnesium stearate was sieved through #20 screen, added and the blend mixed for further 2 minutes. The final blend was then filled into capsules using a MG2 Futura Encapsulation machine. The capsules were packed into HDPE bottles and induction sealed.

The stability of the capsule formulations (at 40° C. and 75% RH) in a HDPE bottle, induction sealed with no dessicant is shown in Table 13.

TABLE 13

Formulation Stability

| Time | Amount of De-BOC (% w/w) Capsule I |
|---|---|
| Initial | Not Detected |
| 2 weeks | Not Detected |
| 1 Month | Not Detected |
| 2 Months | Not Detected |
| 3 Months | 0.124 |

Example 1F

Capsules containing cariprazine hydrochloride, Starcap 1500 (a mixture of co-processed corn starch and pregelatinized starch) were prepared according to Table 14:

TABLE 14

Composition of Capsule Formulation

| Ingredient | Amount (% w/w) Capsule I (0.5 mg)* |
|---|---|
| Cariprazine hydrochloride | 0.545 |
| Corn starch, pregelatinized starch (Starcap 1500) | 98.455 |
| Magnesium stearate | 1.000 |
| Total | 100.0 |

*amount of cariprazine free base

The Starcap1500 and cariprazine were sieved through a #20 sieve and mixed in a V-shell blender for 20 minutes by 5 step geometric mixing using an Intensifier bar in the final step. The magnesium stearate was sieved through #20 screen, added and the blend mixed for further 2 minutes. The final blend was then filled into capsules using a MG2 Futura Encapsulation machine. The capsules were packed into HDPE bottles and induction sealed.

The stability of the capsule formulations (at 40° C. and 75% RH) in a HDPE bottle, induction sealed with no dessicant is shown in Table 15.

TABLE 15

Formulation Stability

| Time | Amount of De-BOC (% w/w) Capsule I |
|---|---|
| Initial | Not Detected |
| 2 weeks | Not Detected |
| 1 Month | Not Detected |
| 2 Months | 0.08 |
| 3 Months | 0.118 |

Example 2

Preparation of a Stable Tablet Formulations Containing Cariprazine

Example 2A

Tablet formulations containing cariprazine hydrochloride and lactose monohydrate were prepared as shown in Table 16.

TABLE 16

Tablet Formulations

| Ingredient | Function | Amount (% w/w) | Amount (mg/tablet) Tablet I 0.5 mg* | Tablet II 2.0 mg* | Tablet III 2.5 mg* |
|---|---|---|---|---|---|
| Lactose monohydrate | Filler | 88.971 | 62.28 | 249.12 | 311.4 |
| Cariprazine hydrochloride | Active | 0.779 | 0.545 | 2.18 | 2.725 |
| Talc USP | Glidant | 2.5 | 1.75 | 7.0 | 8.75 |
| Collodial silicon dioxide | Glidant | 1.0 | 0.7 | 2.8 | 3.5 |

TABLE 16-continued

| Tablet Formulations | | | | | |
|---|---|---|---|---|---|
| | | Amount | Amount (mg/tablet) | | |
| Ingredient | Function | (% w/w) | Tablet I 0.5 mg* | Tablet II 2.0 mg* | Tablet III 2.5 mg* |
| Sodium starch glycolate | Dis-integrant | 4.0 | 2.8 | 11.2 | 14.0 |
| Hydroxypropyl cellulose | Binder | 2.0 | 1.4 | 5.6 | 7.0 |
| Magnesium stearate | Lubricant | 0.75 | 0.525 | 2.1 | 2.625 |
| Total | | 100.00 | 70 | 280 | 350 |

*amount of cariprazine free base

All ingredients except the magnesium stearate were sieved through a #20 sieve and mixed in a V-shell blender for 10 minutes. Mixing was continued for a further 10 minutes using an Intensifier bar in the final step. The magnesium stearate was sieved through #20 screen, added and the blend mixed for further 2 minutes. The final blend was then compressed into tablets using a Korsch PH106 compression machine. The tablets were packed into HDPE bottles and induction sealed.

The stability of the tablet formulations (at 40° C. and 75% RH) in a HDPE bottle, induction sealed with no dessicant is shown in Table 17.

TABLE 17

| Formulation Stability | | | |
|---|---|---|---|
| | Amount of De-BOC (% w/w) | | |
| Time | Tablet I | Tablet II | Tablet III |
| Initial | 0.07 | Not Detected | 0.06 |
| 1 Month | 0.05 | Not Detected | Not Detected |
| 2 Months | 0.08 | Not Detected | 0.05 |
| 3 Months | 0.06 | Not Detected | 0.07 |
| 6 Months | 0.08 | Not Detected | 0.08 |

The dissolution rates for Tablet I after storage at 40° C. and 75% RH in a HDPE bottle, induction sealed with no dessicant is shown in Table 18.

TABLE 18

| Dissolution Rates | | | | | |
|---|---|---|---|---|---|
| Time | % Released | | | | |
| (mins) | Initial | 1 Month | 2 Months | 3 Months | 6 Months |
| 0 | 0 | 0 | 0 | 0 | 0 |
| 5 | 60 | 65 | 62 | 68 | 67 |
| 10 | 88 | 87 | 84 | 93 | 98 |
| 15 | 91 | 89 | 87 | 96 | 100 |
| 30 | 90 | 90 | 89 | 97 | 104 |
| 45 | 92 | 91 | 90 | 98 | 100 |
| 60 | 92 | 91 | 90 | 98 | 100 |

The dissolution rates for Tablet II after storage at 40° C. and 75% RH in a HDPE bottle, induction sealed with no dessicant is shown in Table 19.

TABLE 19

| Dissolution Rates | | | | | |
|---|---|---|---|---|---|
| Time | % Released | | | | |
| (mins) | Initial | 1 Month | 2 Months | 3 Months | 6 Months |
| 0 | 0 | 0 | 0 | 0 | 0 |
| 15 | 90 | 89 | 86 | 92 | 88 |
| 30 | 95 | 94 | 96 | 96 | 91 |
| 45 | 97 | 96 | 97 | 97 | 92 |
| 60 | 98 | 97 | 98 | 99 | 93 |

The dissolution rates for in Tablet III after storage at 40° C. and 75% RH in a HDPE bottle, induction sealed with no dessicant is shown in Table 20.

TABLE 20

| Dissolution Rates | | | | | |
|---|---|---|---|---|---|
| Time | % Released | | | | |
| (mins) | Initial | 1 Month | 2 Months | 3 Months | 6 Months |
| 0 | 0 | 0 | 0 | 0 | 0 |
| 5 | 64 | 75 | 68 | 76 | 77 |
| 10 | 86 | 93 | 89 | 92 | 90 |
| 15 | 91 | 97 | 93 | 96 | 94 |
| 30 | 97 | 100 | 97 | 99 | 95 |
| 45 | 98 | 101 | 98 | 100 | 96 |
| 60 | 99 | 102 | 100 | 100 | 96 |

Example 2B

Tablet formulations containing cariprazine hydrochloride and lactose monohydrate were prepared as shown in Table 21.

TABLE 21

| Tablet Formulations | | | | |
|---|---|---|---|---|
| | | | Amount (mg/tablet) | |
| Ingredient | Function | Amount (% w/w) | Tablet I 2.5 mg* | Tablet II 12.5 mg* |
| Lactose monohydrate | Filler | 85.855 | 60.098 | 300.49 |
| Cariprazine hydrochloride | Active | 3.895 | 2.727 | 13.635 |
| Talc USP | Glidant | 1.0 | 0.7 | 3.5 |
| Collodial silicon dioxide | Glidant | 2.5 | 1.75 | 8.75 |
| Sodium starch glycolate | Disintegrant | 4.0 | 2.8 | 14.0 |
| Hydroxypropyl cellulose | Binder | 2.0 | 1.4 | 7.0 |
| Magnesium stearate | Lubricant | 0.75 | 0.525 | 2.625 |
| Total | | 100.00 | 70 | 350 |

*amount of cariprazine free base

All ingredients except the magnesium stearate were sieved through a #20 sieve and mixed in a V-shell blender for 10 minutes. Mixing was continued for a further 10 minutes using an Intensifier bar in the final step. The magnesium stearate was sieved through #20 screen, added and the blend mixed for further 2 minutes. The final blend was then compressed into tablets using a Korsch PH106 compression machine. The tablets were packed into HDPE bottles and induction sealed.

The stability of the tablet formulations (at 40° C. and 75% RH) in a HDPE bottle, induction sealed with no dessicant is shown in Table 22.

TABLE 22

Formulation Stability

| Time | Amount of De-BOC (% w/w) Tablet I | Tablet II |
|---|---|---|
| Initial | 0.0265 | Not Detected |
| 1 Month | 0.02 | Not Detected |
| 2 Months | Not Detected | Not Detected |
| 3 Months | Not Detected | Not Detected |
| 6 Months | Not Detected | Not Detected |

The dissolution rates for Tablet I after storage at 40° C. and 75% RH in a HDPE bottle, induction sealed with no dessicant is shown in Table 23.

TABLE 23

Dissolution Rates

| Time | % Released | | | | |
|---|---|---|---|---|---|
| (mins) | Initial | 1 Month | 2 Months | 3 Months | 6 Months |
| 0 | 0 | 0 | 0 | 0 | 0 |
| 5 | 67 | 61 | 58 | 59 | Not tested |
| 10 | 95 | 90 | 89 | 91 | Not tested |
| 15 | 99 | 95 | 94 | 95 | 96 |
| 30 | 101 | 97 | 96 | 96 | 101 |
| 45 | 102 | 98 | 96 | 97 | 101 |
| 60 | 103 | 98 | 97 | 98 | 102 |

The dissolution rates for Tablet II after storage at 40° C. and 75% RH in a HDPE bottle, induction sealed with no dessicant is shown in Table 24.

TABLE 24

Dissolution Rates

| Time | % Released | | | | |
|---|---|---|---|---|---|
| (mins) | Initial | 1 Month | 2 Months | 3 Months | 6 Months |
| 0 | 0 | 0 | 0 | 0 | 0 |
| 5 | 57 | 68 | 55 | 57 | Not tested |
| 10 | 93 | 89 | 83 | 86 | Not tested |
| 15 | 101 | 93 | 91 | 92 | 97 |
| 30 | 105 | 97 | 96 | 96 | 101 |
| 45 | 107 | 98 | 98 | 97 | 101 |
| 60 | 108 | 99 | 99 | 98 | 102 |

Example 2C

Tablets containing cariprazine hydrochloride and sodium carbonate as a buffering agent were prepared according to Table 25:

TABLE 25

Tablet Formulations

| Ingredient | Function | Amount (% w/w) |
|---|---|---|
| Microcrystalline cellulose (Avicel PH102) | Filler | 86.221 |

TABLE 25-continued

Tablet Formulations

| Ingredient | Function | Amount (% w/w) |
|---|---|---|
| Cariprazine hydrochloride | Active | 0.779 |
| Talc USP | Glidant | 3.000 |
| Collodial silicon dioxide | Glidant | 1.000 |
| Sodium starch glycolate | Disintegrant | 3.000 |
| Magnesium stearate | Lubricant | 1.000 |
| Sodium carbonate | pH modifier | 5.000 |
| Total | | 100.000 |

All ingredients except the magnesium stearate were sieved through a #20 sieve and mixed in a V-shell blender for 15 minutes. The magnesium stearate was sieved through #20 screen, added and the blend mixed for further 2 minutes. The final blend was then compressed into tablets using a Korsch PH106 compression machine. The tablets were packed into HDPE bottles and induction sealed.

The stability of the tablet formulations (at 40° C. and 75% RH) in a HDPE bottle, induction sealed with no dessicant is shown in Table 26.

TABLE 26

Formulation Stability

| Time | Amount of De-BOC (% w/w) |
|---|---|
| Initial | Not Detected |
| 2 Weeks | Not Detected |
| 1 Month | 0.090 |
| 2 Months | 0.102 |
| 3 Months | 0.176 |
| 6 Months | 0.165 |

The amount of De-BOC present in formulations containing differing amounts of sodium carbonate (stored for 3 months at 40° C., 75% RH in sealed 60 cc HDPE bottles with no desiccant) is shown in Table 27. Slurries were prepared by taking a tablet and dispersing it in the correct volume of deionized water needed to prepare a suspension containing 2% solids. The pH of the slurry was then measured using pH meter.

TABLE 27

Formulation Stability

| Amount of Sodium Carbonate (% w/w) | pH (2% slurry) | Amount of De-Boc after 3 months at 40 C./75% RH (% w/w) |
|---|---|---|
| 1.0 | 10.4 | 0.36 |
| 5.0 | 10.9 | 0.17 |
| 10.0 | 11.1 | 0.14 |

Example 3

Comparison Examples

Additional tablets containing cariprazine hydrochloride and other excipients were prepared according to Table 28:

TABLE 28

| Tablet Formulations | | | | | | | | | | | |
|---|---|---|---|---|---|---|---|---|---|---|---|
| Ingredient (% w/w) | Tablet 1 | Tablet 2 | Tablet 3 | Tablet 4 | Tablet 5 | Tablet 6 | Tablet 7 | Tablet 8 | Tablet 9 | Tablet 10 | Tablet 11 |
| Cariprazine hydrochloride | 0.779 | 0.779 | 0.779 | 0.779 | 0.779 | 0.779 | 0.779 | 0.779 | 0.779 | 0.779 | 0.779 |
| Talc USP | 3.000 | 3.0 | 3.0 | 3.0 | 3.0 | 3.0 | 3.0 | 3.0 | 3.0 | 3.0 | 3.0 |
| Sodium starch glycolate | 5.000 | 5.0 | 0.5 | 0.5 | 3.0 | 0.5 | 3.0 | 0.5 | 0.5 | 3.0 | 3.0 |
| Magnesium stearate | 1.000 | 1.0 | 1.0 | 1.0 | 1.0 | 1.0 | 1.0 | 1.0 | 1.0 | 1.0 | 1.0 |
| Aerosil 200VV | 0.700 | 1.0 | 1.0 | 1.0 | 1.0 | 1.0 | 1.0 | 1.0 | 1.0 | 1.0 | 1.0 |
| Prosolv SMCC90 | 89.521 | — | — | — | — | — | — | — | — | — | — |
| Avicel PH102 | — | 89.221 | 62.721 | 62.721 | 81.221 | 93.721 | 88.721 | — | — | 91.121 | 91.201 |
| Starch 1500 | — | — | 31 | — | — | | — | — | 93.721 | — | — |
| Dicalcium phosphate dihydrate | — | — | — | 31.0 | — | — | — | — | — | — | — |
| Magnesium oxide | — | — | — | — | 10.0 | — | — | — | — | — | — |
| Syloid 63FP | — | — | — | — | — | — | 2.5 | — | — | — | — |
| Butylated Hydroxyanisol | — | — | — | — | — | — | — | — | — | — | 0.01 |
| Butylated Hydroxytoluene | — | — | — | — | — | — | — | — | — | — | 0.01 |
| EDTA | — | — | — | — | — | — | — | — | — | 0.1 | — |
| Avicel PH112 (Low Moisture) | — | — | — | — | — | — | — | 93.721 | — | — | — |
| Total | 100 | 100 | 100 | 100 | 100 | 100 | 100 | 100 | 100 | 100 | 100 |

All ingredients except the magnesium stearate were sieved through a #20 sieve and mixed in a V-shell blender for 15 minutes. The magnesium stearate was sieved through #20 screen, added and the blend mixed for further 2 minutes. The final blend was then compressed into tablets using a Korsch PH106 compression machine. The tablets were packed into HDPE bottles and induction sealed.

The stability of the tablet formulations described in Table 29 (stored at 40° C. and 75% RH in 60 cc HDPE bottles, induction sealed with no dessicant) is shown in Table 29.

TABLE 29

| Formulation Stability | | | | | | | | | | | |
|---|---|---|---|---|---|---|---|---|---|---|---|
| | Amount of De-BOC (% w/w) | | | | | | | | | | |
| Time | Tablet 1 | Tablet 2 | Tablet 3 | Tablet 4 | Tablet 5 | Tablet 6 | Tablet 7 | Tablet 8 | Tablet 9 | Tablet 10 | Tablet 11 |
| Initial | 0.058 | 0.052 | ND | ND | ND | ND | ND | ND | ND | ND | ND |
| 2 Weeks | 0.344 | 0.273 | 0.119 | 0.194 | 0.136 | 0.196 | 0.069 | 0.102 | 0.076 | 0.095 | 0.093 |
| 1 Month | 0.617 | 0.483 | 0.192 | 0.342 | 0.350 | 0.749 | 0.139 | 0.369 | 0.36 | 0.245 | 0.226 |
| 2 Months | 1.318 | 0.925 | 0.720 | 0.799 | 0.464 | 1.411 | 0.312 | 0.512 | 0.496 | 0.500 | 0.474 |
| 3 Months | 2.66 | 1.765 | Not Tested | Not Tested | Not Tested | Not Tested | Not Tested | 0.755 | 0.760 | Not Tested | Not Tested |

As can be seen from Table 30, the amount of De-Boc present in each of these tablet formulations at 2 months is greater than for the capsule and tablet formulations of the present invention described in Examples 1 and 2.

Example 4

A Double-Blind Placebo Controlled Single Dose Study Conducted in Healthy Male Volunteers A double-blind, placebo controlled single dose study of the pharmacokinetic parameters of cariprazine (capsules) in healthy male volunteers was conducted. The design of the study is shown in Table 30.

TABLE 30

| Study Design | | | | | | |
|---|---|---|---|---|---|---|
| Group | Number of Subjects Receiving Active Drug | Period | Dose (mg) | Condition | Wash-Out Interval Before Period 2 | PK Blood Sampling |
| I | 6 | 1 | 1 | Fasted | | 0-168 h |
| II | 6 | 1 | 2.5 | Fasted | | 0-336 h |

TABLE 30-continued

| Study Design | | | | | | |
|---|---|---|---|---|---|---|
| Group | Number of Subjects Receiving Active Drug | Period | Dose (mg) | Condition | Wash-Out Interval Before Period 2 | PK Blood Sampling |
| I | 6 | 2 | 2 | Fasted | ~2 weeks | 0-672 h |
| II | 6 | 2 | 1.5 | Fasted | ~4 weeks | 0-336 h |
| III | 6 | 1 | 0.5 | Fasted | | 0-168 h |

The composition of the capsules is given below in Table 31.

TABLE 31

Capsule Composition

| Ingredient | Amount (mg) 0.5 mg Capsule | 2.5 mg Capsule | 12.5 mg Capsule |
|---|---|---|---|
| Cariprazine hydrochloride | 0.543 | 2.713 | 13.563 |
| Microcrystalline cellulose | 59.457 | 58.177 | 51.690 |
| Calcium hydrogen phosphate, anhydrous | 40.00 | 39.110 | 34.747 |

The mean pharmacokinetic parameters observed after administration of a single dose of 0.5 to 2.5 mg cariprazine are shown below in Table 32.

TABLE 32

Mean Pharmacokinetic Parameters

| Treatment Group | Period | Dose (mg) | $C_{max}$, (ng/mL) | $AUC_{0-168}$, (ng/mL * h) | $T_{max}$, (h) | $T_{1/2}$ (h) |
|---|---|---|---|---|---|---|
| III | 1 | 0.5 | 0.14 | 14.09 | 6 | 216.7 |
| I | 1 | 1 | 0.76 | 35.36 | 3 | 185.3 |
| II | 2 | 1.5 | 1.19 | 46.66 | 3 | 129.9 |
| I | 2 | 2 | 2.53 | 95.33 | 3 | 130.0 |
| II | 1 | 2.5 | 2.50 | 97.46 | 4 | 138.5 |

Mean maximum plasma concentrations ($C_{max}$) were generally obtained within about 3 to about 6 hours of dosing. $T_{max}$, values are about 3 to about 6 hours.

The pharmacokinetics of trans-1{4-[2-[4-(2,3-dichlorophenyl)-piperazin-1-yl]-ethyl]-cyclohexyl}-3,3-dimethylurea hydrochloride over the single-dose range of 0.5 mg to 2.5 mg suggest approximate dose proportionality of exposure relative to mean AUC. Linear calculated pharmacokinetic parameters (based on the 2.0 mg data (Table 35, 80% of AUClast, Treatment I) for dosages greater than 2.0 mg and on the 0.5 mg data for dosages lower than 0.5 mg (Table 33) are shown in Table 33.

TABLE 33

Linear Calculated Pharmacokinetic Parameters

| Dose (mg) | Mean $C_{max}$ (ng/mL) | Mean $AUC_{0-168}$ (ng/mL * h) |
|---|---|---|
| 0.1 | 0.03 | 2.82 |
| 0.25 | 0.09 | 1.05 |
| 3 | 3.80 | 96.8 |
| 4.5 | 5.70 | 145.2 |
| 5 | 6.33 | 161.4 |
| 6 | 7.60 | 193.6 |
| 7.5 | 9.50 | 242.1 |
| 9 | 11.39 | 290.4 |
| 12.5 | 15.83 | 403.5 |
| 15 | 18.99 | 484.2 |

One skilled in the art with the benefit of this disclosure may readily determine pharmacokinetic parameters for any specific dosage of cariprazine used in a formulation.

Example 5

A Single-Center, Randomized, Open-Label, Parallel-Group Single-Dose Study

The objectives of this study were (i) to assess the effect of food on the oral bioavailability of cariprazine (2-mg tablet), (ii) to assess the effect of gender on the oral bioavailability of cariprazine after a single oral dose (2-mg tablet), and (iii) to evaluate the pharmacokinetics of cariprazine and its metabolites after an oral dose (2-mg tablet).

Methodology

This clinical study was conducted as a single-center, randomized, open-label, parallel-group single-dose study. A total of 42 healthy male and female patients aged 18-45 years were selected, with an approximate male-to-female ratio of 1:1.

Dosing occurred in two treatment sessions (Treatment 1 and Treatment 2) separated by 5 to 7 days. The subjects were randomized with ~1:1 male-female ratio to receive one of the following two treatments:

Treatment 1:

Single oral dose of one 2-mg cariprazine tablet under fasted conditions (12 female, 11 male subjects)

Treatment 2:

Single oral dose of one 2-mg cariprazine tablet under fed conditions (10 female, 9 male subjects)

Subjects were given the study drug with 240 mL of water in the clinic under fed/fasted conditions at 0800 hours on Day 1. Subjects taking Treatment 1 underwent a 10-hour overnight fast before dosing on Day 1 and continued fasting for an additional 4 hours postdose. Subjects taking Treatment 2 underwent a 10-hour overnight fast before eating a US Food and Drug Administration standardized high-fat breakfast at 0730 hours on Dosing Day 1.

This study was 30 days in duration (Day −1 through the last pharmacokinetic (PK) blood sample collection on Day 29).

Patient Evaluations

Vital Signs/Adverse Event Assessment

Heart rate and blood pressure were measure in the supine position (the subject lying down for at least 5 minutes prior to testing) on the same arm throughout the study and before any corresponding blood sample was collected. In addition to the Screening and End-of-Study measurements, vital signs (BP and pulse) were measured at:

Day 1: (0.0 (predose), 2, 4, 8 and 12 hours postdose)

Day 2: 25 hours after Day 1 dose administration

Day 3: 48 hours after Day 1 dose administration

Day 5: 96 hours after Day 1 dose administration

Blood Sampling

Blood sampling was performed at the following times to determine cariprazine plasma concentrations:

0.0 (predose), 0.5, 1, 2, 3, 4, 6, 8, 12, 24, 36, 48, 72, 96, 168, 336, 504 and 672 hours postdose.

The mean pharmacokinetic parameters observed during the study are presented in Table 34.

TABLE 34

Mean Pharmacokinetic Parameters

| Treatment Group | $C_{max}$ (ng/mL) | $AUC_{last}$ (ng · h/mL) | AUC∞-obs (ng · h/mL) | Tmax (h) | T½ (h) |
|---|---|---|---|---|---|
| Treatment 1 (Fasted) | 1.99 | 80.69 | 89.87 | 4.91 | 202.60 |

TABLE 34-continued

| Mean Pharmacokinetic Parameters | | | | | |
|---|---|---|---|---|---|
| Treatment Group | $C_{max}$ (ng/mL) | $AUC_{last}$ (ng · h/mL) | AUC∞-obs (ng · h/mL) | Tmax (h) | T½ (h) |
| Treatment 1 (Fed) | 1.72 | 89.22 | 96.96 | 9.21 | 198.33 |

Example 6

A Multiple Dose Study Conducted in Healthy Male Volunteers

Thirty-two healthy male subjects (mean age=24.9 years) were randomized into 4 groups (I-IV). In each group, 2 subjects received placebo and 6 subjects received one of the following treatments:

(I) 7 doses of 0.5 mg cariprazine administered every other day;

(II) 14 doses of 0.5 mg cariprazine every day;

(III) 2 doses of 0.5 mg cariprazine followed by 12 doses of 1.0 mg cariprazine every day; and (IV) 21 doses of 1.0 mg cariprazine every day.

Plasma samples were analyzed for cariprazine by a validated LC-MS/MS assay (Internal Standards: deuterated compounds; Sample preparation: Liquid-liquid extraction after alkalization; Sample Volume: 1 mL; Calibration Range: 0.05-25 ng/mL; Inonization: +ESI with MRM mode).

The design of the study is shown below in Table 35.

TABLE 35

| Study Design | | | | | | | | |
|---|---|---|---|---|---|---|---|---|
| | | | | | | PK Blood Sampling | | |
| Group | Number of Subjects Receiving Active Drug | Frequency of dosing | Dose, mg | Days | Condition | PK Profile After First Dose | Predose Samples | PK Profile After Last Dose |
| I | 6 | once every other day | 0.5 | 1, 3, 5, 7, 9, 11, 13 | Fasted | 0-48 h | Days 3, 5, 7, 9, 11 | 0-3 weeks |
| II | 6 | once daily | 0.5 | 1-14 | Fasted | 0-24 h | Days 2, 3, 4, 5, 7, 9, 11, 13 | 0-9 weeks |
| III | 6 | once daily | 0.5/1 | 1-2 (0.5 mg) 3-14 (1 mg) | Fasted | 0-24 h | Days 2, 3, 4, 5, 7, 9, 11, 13 | 0-9 weeks |
| IV | 6 | once daily | 1 | 1-21 | Fasted | 0-24 h | Days 2, 3, 5, 8, 11, 14, 16, 18, 19, 20 | 0-9 weeks |

The mean pharmacokinetic parameters observed are shown below in Table 36.

TABLE 36

| Mean Pharmacokinetic Parameters | | | |
|---|---|---|---|
| Treatment Group | $C_{max}$, ng/mL | $t_{max}$, h | $AUC_{0-\tau}$, ng/mL * h |
| I | 1.034 (22.3) | 4 (3-6) | 32.9 (21.6) |
| II | 1.418 (18.0) | 3.5 (2-4) | 25.0 (22.8) |

TABLE 36-continued

| Mean Pharmacokinetic Parameters | | | |
|---|---|---|---|
| Treatment Group | $C_{max}$, ng/mL | $t_{max}$, h | $AUC_{0-\tau}$, ng/mL * h |
| III | 3.193 (25.9) | 4 (2-4) | 53.6 (30.6) |
| IV | 3.897 (18.9) | (2-3) | 56.8 (18.1) |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

We claim:

[1. A method of treating a condition selected from the group consisting of schizophrenia, bipolar disorder, acute mania, and depression, the method comprising administering to a patient in need thereof a solid oral pharmaceutical formulation comprising from about 0.05 to about 9 mg trans-1{4-[2-[4-(2,3-dichlorophenyl)-piperazin-1-yl]-ethyl]-cyclohexyl}-3,3-dimethyl-urea, or a pharmaceutically acceptable salt thereof, and an excipient having low water activity selected from the group consisting of pregelatinized starch, mannitol, anhydrous calcium hydrogen phosphate, and mixtures thereof, wherein the formulation provides an in vivo plasma profile comprising a mean $C_{max}$ of less than about 26.3 ng/mL, a mean $AUC_0$-∞ of more than about 2 ng·hr/mL and a mean $T_{max}$ of about 3 or more hours, wherein the formulation has a dissolution rate of more than about 80% within about the first 60 minutes following administration of the composition to the patient; and wherein the formulation has a pH in the range of about 9.0 to about 12.0.]

[2. The method of claim 1, wherein the formulation comprises about 1.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, and provides an in vivo plasma profile comprising a mean $C_{max}$ of less than about 2.7 ng/mL and a mean $T_{max}$ of about 3 or more hours.]

[3. The method of claim 1, wherein the formulation comprises about 3 mg trans-1{4-[2-[4-(2,3-dichlorophenyl)-piperazin-1-yl]-ethyl]-cyclohexyl}-3,3-dimethyl-urea, or a pharmaceutically acceptable salt thereof, and provides an in vivo plasma profile comprising a mean $C_{max}$ of less than about 5.3 ng/mL and a mean $T_{max}$ of about 3 or more hours.]

[4. The method of claim 1, wherein the formulation comprises about 4.5 mg trans-1{4-[2-[4-(2,3-dichlorophenyl)-piperazin-1-yl]-ethyl]-cyclohexyl}-3,3-dimethyl-urea, or a pharmaceutically acceptable salt thereof, and provides an in vivo plasma profile comprising a mean $C_{max}$ of less than about 7.9 ng/mL and a mean $T_{max}$ of about 3 or more hours.]

[5. The method of claim 1, wherein the formulation comprises about 6 mg trans-I{4-[2-[4-(2,3-dichlorophenyl)-piperazin-I-yl]-ethyl]-cyclohexyl}-3,3-dimethyl-urea, or a pharmaceutically acceptable salt thereof, and provides an in vivo plasma profile comprising a mean $C_{max}$ of less than about 10.5 ng/mL and a mean $T_{max}$ of about 3 or more hours.]

[6. The method of claim 1, wherein the formulation comprises about 9 mg trans-I{4-[2-[4-(2,3-dichlorophenyl)-piperazin-I-yl]-ethyl]-cyclohexyl}-3,3-dimethyl-urea, or a pharmaceutically acceptable salt thereof, and provides an in vivo plasma profile comprising a mean $AUC_0$-∞ of more than about 180 ng·hr/mL and a mean $T_{max}$ of about 3 or more hours.]

[7. The method of claim 1, wherein the formulation comprises about 0.5 mg trans-I{4-[2-[4-(2,3-dichlorophenyl)-piperazin-I-yl]-ethyl]-cyclohexyl}-3,3-dimethyl-urea, or a pharmaceutically acceptable salt thereof, and provides an in vivo plasma profile comprising a mean $C_{max}$ of less than about 0.9 ng/mL and a mean $T_{max}$ of about 3 or more hours.]

[8. The method of claim 1, wherein the excipient comprises pregelatinized starch.]

[9. The method of claim 1, wherein the excipient comprises mannitol.]

[10. The method of claim 1, wherein the excipient comprises anhydrous calcium hydrogen phosphate.]

*11. A method of treating a condition selected from the group consisting of schizophrenia, bipolar disorder, acute mania, and depression, the method comprising administering to a patient in need thereof a solid oral pharmaceutical formulation comprising about 1.5 mg, about 3 mg, about 4.5 mg, or about 6 mg, of trans-1 {4-[2-[4-(2,3-dichlorophenyl)-piperazin-1-yl]-ethyl]-cyclohexyl}-3,3-dimethyl-urea, or a pharmaceutically acceptable salt thereof, and a pregelatinized starch.*

*12. The method of claim 11, wherein the solid oral pharmaceutical formulation comprises about 1.5 mg trans-1 {4-[2-[4-(2,3-dichlorophenyl)-piperazin-1-yl]-ethyl]-cyclohexyl}-3,3-dimethyl-urea, or a pharmaceutically acceptable salt thereof.*

*13. The method of claim 11, wherein the solid oral pharmaceutical formulation comprises about 3.0 mg trans-1 {4-[2-[4-(2,3-dichlorophenyl)-piperazin-1-yl]-ethyl]-cyclohexyl}-3,3-dimethyl-urea, or a pharmaceutically acceptable salt thereof.*

*14. The method of claim 11, wherein the solid oral pharmaceutical formulation comprises about 4.5 mg trans-1 {4-[2-[4-(2,3-dichlorophenyl)-piperazin-1-yl]-ethyl]-cyclohexyl}-3,3-dimethyl-urea, or a pharmaceutically acceptable salt thereof.*

*15. The method of claim 11, wherein the solid oral pharmaceutical formulation comprises about 6.0 mg trans-1 {4-[2-[4-(2,3-dichlorophenyl)-piperazin-1-yl]-ethyl]-cyclohexyl}-3,3-dimethyl-urea, or a pharmaceutically acceptable salt thereof.*

* * * * *